(12) United States Patent
Biedermann et al.

(10) Patent No.: US 12,714,472 B2
(45) Date of Patent: Aug. 25, 2026

(54) BONE ANCHORING DEVICE

(71) Applicant: BIEDERMANN TECHNOLOGIES GMBH & CO. KG, Donaueschingen (DE)

(72) Inventors: Lutz Biedermann, VS-Villingen (DE); Timo Biedermann, Trossingen (DE)

(73) Assignee: BIEDERMANN TECHNOLOGIES GMBH & CO. KG, Donaueschingen (DE)

( * ) Notice: Subject to any disclaimer, the term of this patent is extended or adjusted under 35 U.S.C. 154(b) by 0 days.

(21) Appl. No.: 19/416,818

(22) Filed: Dec. 11, 2025

(65) Prior Publication Data

US 2026/0165747 A1 Jun. 18, 2026

Related U.S. Application Data

(60) Provisional application No. 63/733,140, filed on Dec. 12, 2024.

(30) Foreign Application Priority Data

Dec. 12, 2024 (EP) .................................... 24219554

(51) Int. Cl.
*A61B 17/70* (2006.01)

(52) U.S. Cl.
CPC ...... *A61B 17/7037* (2013.01); *A61B 17/7032* (2013.01)

(58) Field of Classification Search
CPC ............ A61B 17/7037; A61B 17/7035; A61B 17/7032; A61B 17/7038
See application file for complete search history.

(56) References Cited

U.S. PATENT DOCUMENTS

| | | | |
|---|---|---|---|
| 7,749,258 B2 | 7/2010 | Biedermann et al. | |
| 7,846,187 B2 | 12/2010 | Jackson | |
| 9,345,516 B2 | 5/2016 | Biedermann et al. | |
| 2004/0204711 A1 | 10/2004 | Jackson | |
| 2008/0147129 A1* | 6/2008 | Biedermann ...... | A61B 17/7032 606/301 |

(Continued)

OTHER PUBLICATIONS

Extended European Search Report for Application No. 24219554.3, dated May 27, 2025, 6 pages.

*Primary Examiner* — Jacqueline T Johanas
(74) *Attorney, Agent, or Firm* — Womble Bond Dickinson (US) LLP

(57) ABSTRACT

A bone anchoring device includes an anchoring element, a receiving part having a first end, a second end, a channel for receiving a rod, an accommodation space at the second end for accommodating a head of the bone anchoring element, and at least one hole that extends transversely through the receiving part, a pressure element configured to engage the rod and the head to lock the head in the receiving part, and a restriction element selectively insertable into the hole. When the pressure element is in the receiving part, the head is insertable from the second end into the receiving part. The restriction element is movable transversely in the hole from a first position where the head is pivotable polyaxially relative to the receiving part, to a second position where the restriction element restricts the pivotability of the head in at least one direction relative to the receiving part.

15 Claims, 18 Drawing Sheets

(56) References Cited

U.S. PATENT DOCUMENTS

| | | | | |
|---|---|---|---|---|
| 2009/0105769 | A1* | 4/2009 | Rock | A61B 17/7038 606/301 |
| 2011/0257690 | A1* | 10/2011 | Rezach | A61B 17/7037 606/302 |
| 2015/0282844 | A1* | 10/2015 | Vedula | A61B 17/8625 606/305 |
| 2017/0049482 | A1 | 2/2017 | Campbell et al. | |
| 2019/0298419 | A1 | 10/2019 | Biedermann et al. | |
| 2021/0282819 | A1* | 9/2021 | Biedermann | A61B 17/7038 |
| 2022/0061892 | A1* | 3/2022 | Jackson | A61B 17/7035 |
| 2022/0125483 | A1 | 4/2022 | Biedermann et al. | |
| 2023/0000527 | A1 | 1/2023 | Bledermann et al. | |
| 2023/0270472 | A1* | 8/2023 | Mcclintock | A61B 17/7037 606/305 |
| 2024/0277383 | A1 | 8/2024 | Biedermann et al. | |

* cited by examiner 5a
5
56
54
55
502
503a
58
503
503b
59
54a
58
5b 5
5a
56
55
55
500a
502
54
503
59
58
58
5b L
5
54a
54
503
503
503a
A
A
503a 5
5a
C
55a
55a
56
51
55
55
500a
500b
54
57a
503
57b
54a
59
59
58
58
5b
52
53
53a

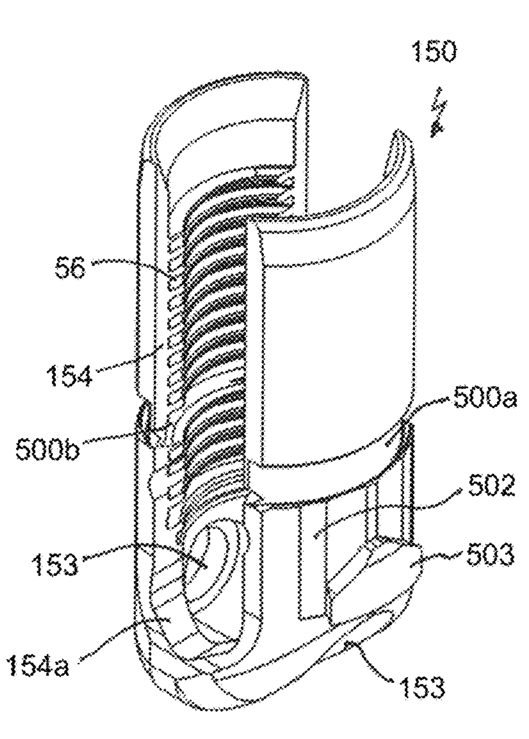
Fig. 24
150
5a
154
505
500a
503
155
155
504
154a
153
5b
153
Fig. 25
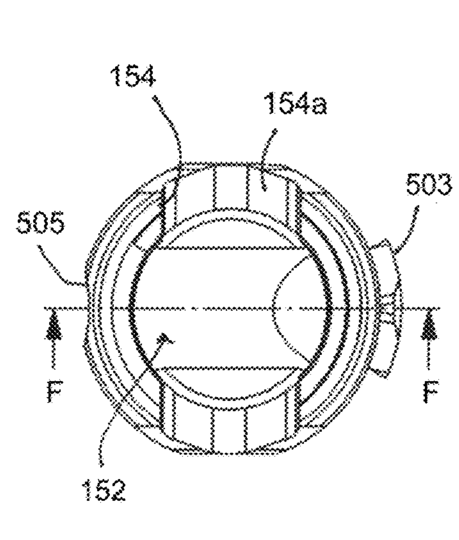
Fig. 26
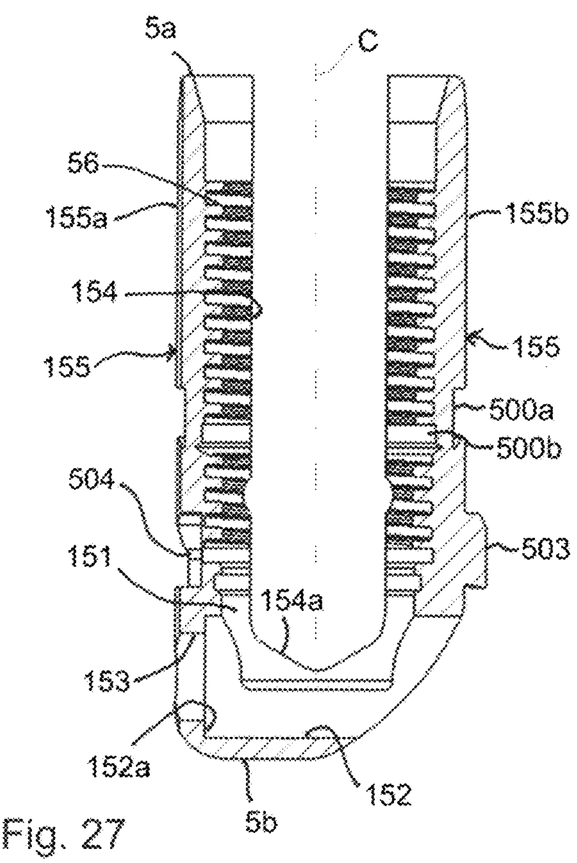
Fig. 27

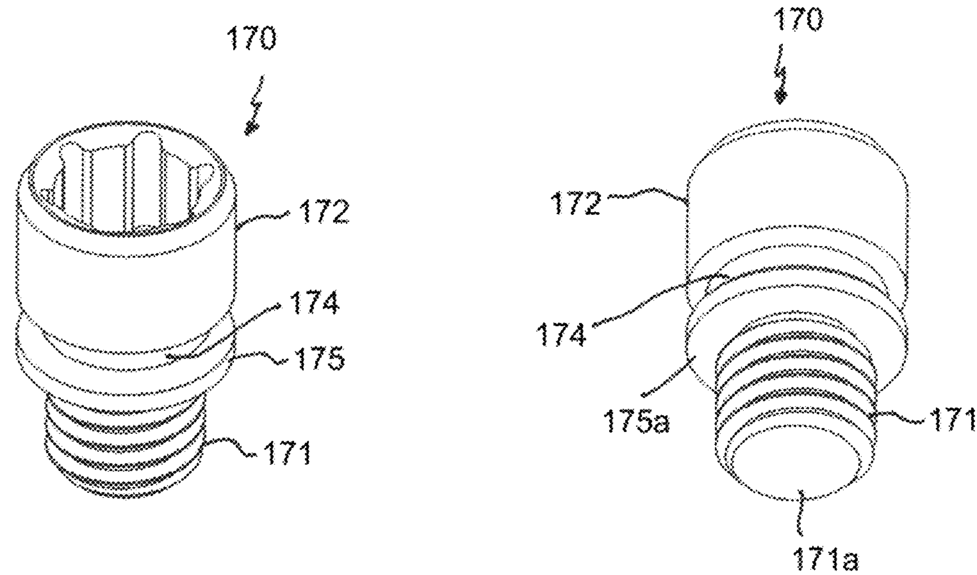
Fig. 28
Fig. 29
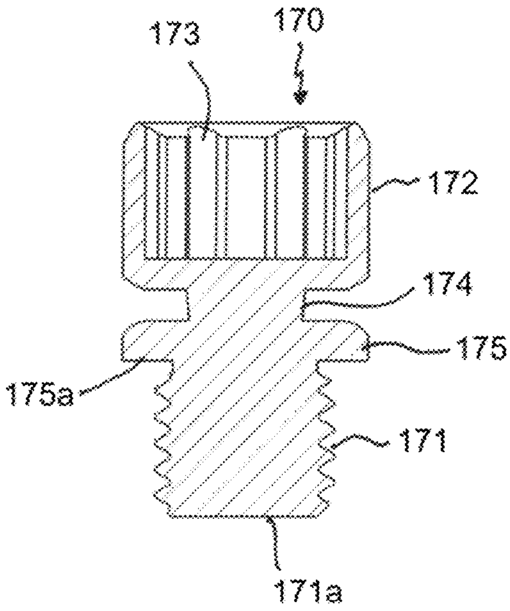
Fig. 30

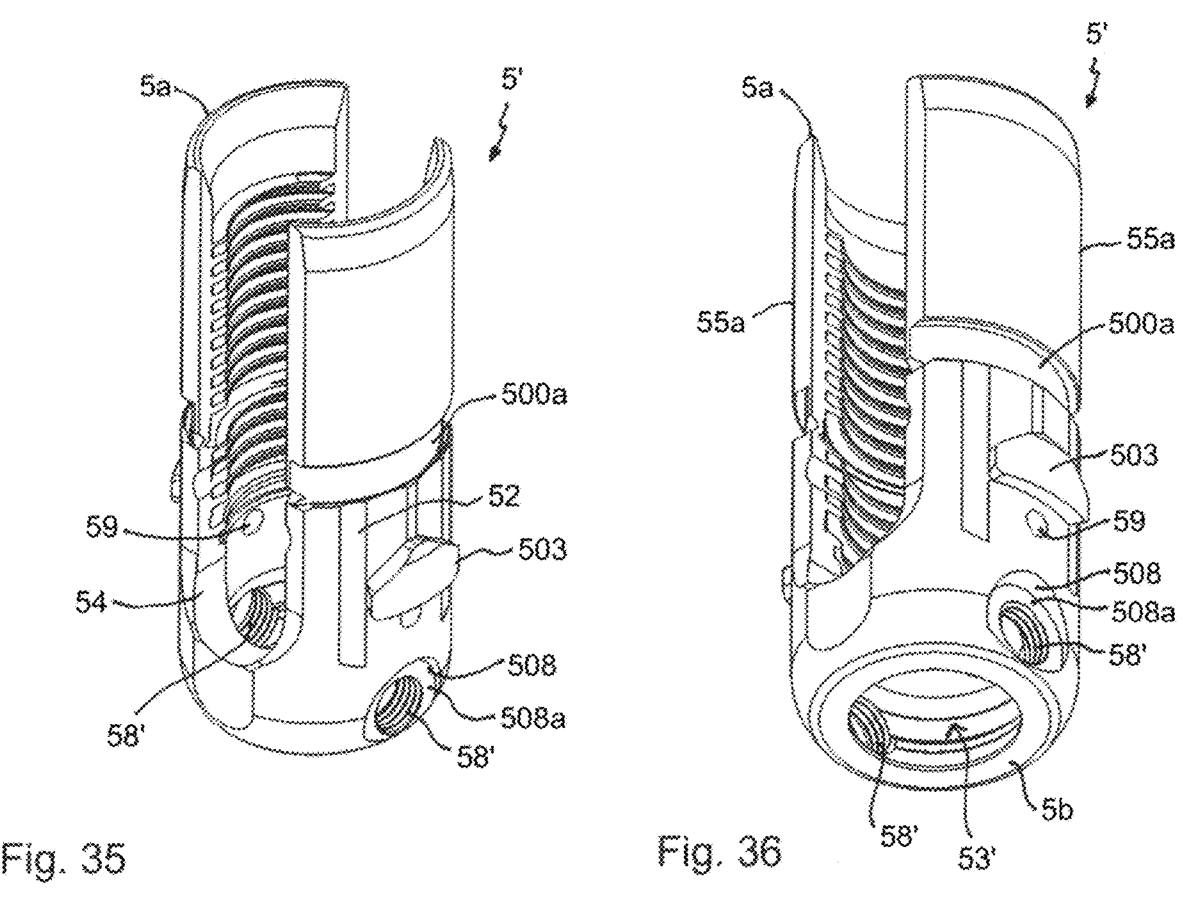
Fig. 35
Fig. 36
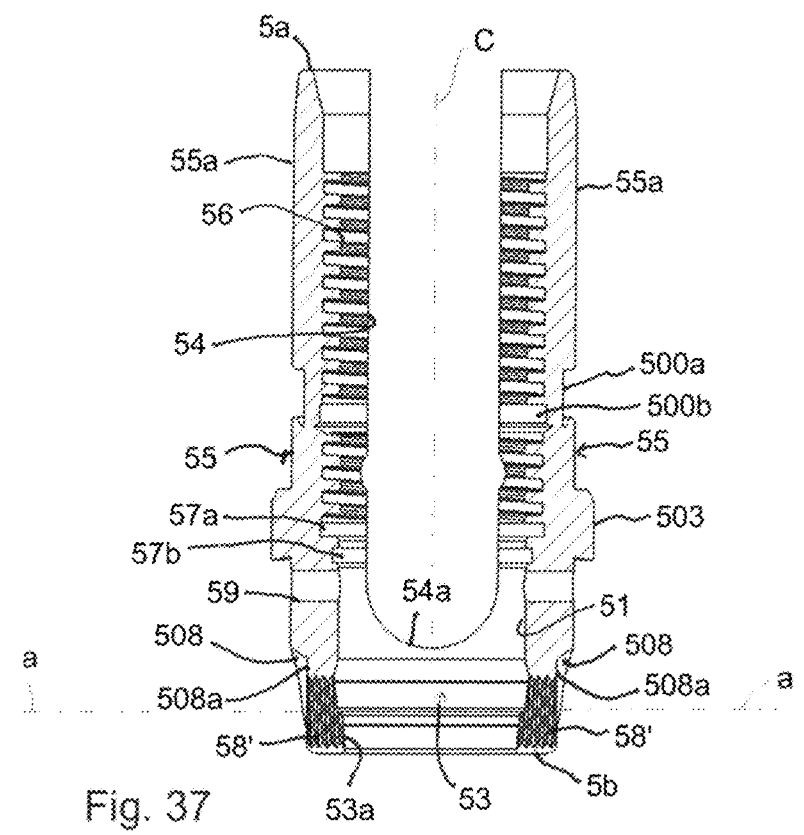
Fig. 37

BONE ANCHORING DEVICE

CROSS-REFERENCE TO RELATED APPLICATION(S)

The present application claims priority to and the benefit of U.S. Provisional Patent Application No. 63/733,140, filed Dec. 12, 2024, the contents of which are hereby incorporated by reference in their entirety, and claims priority from European Patent Application EP 24 219 554.3, filed Dec. 12, 2024, the contents of which are hereby incorporated by reference in their entirety.

BACKGROUND

Field

The present application relates to a bone anchoring device including a bone anchoring element and a receiving part for coupling a rod to the bone anchoring element. In particular, the bone anchoring device is a modular bone anchoring device that can be selectively adapted for various clinical requirements.

Description of Related Art

Bone anchoring devices including a bone anchoring element and a receiving part are used in orthopaedic surgery, in particular in spinal surgery, for coupling a rod to the bone anchoring element when the bone anchoring element is anchored in bone or a vertebra, and where several bone anchoring devices can be connected by the rod. In a polyaxial bone anchoring device, a head of the bone anchoring element is pivotably received in the receiving part, so that the receiving part can assume various angular positions in multiple planes with respect to the bone anchoring element. Thus, a suitable orientation of the bone anchoring element with respect to the rod can be achieved.

For example, a polyaxial bone anchoring device is known from U.S. Pat. No. 9,345,516 B2. The polyaxial bone anchoring device includes an anchoring element having a shaft and a head, a receiving part having a first end and a second end, a bore extending from the first end towards the second end, a seat for receiving the head, and at least one threaded through hole transverse to the bore. The bone anchoring device further includes a pressure element to exert pressure onto the head, such that the head is pivotable and can be locked at an angle relative to the receiving part. The pressure element has at least one hole that is at least partially aligned with the through hole. At least on set screw is threadable into the through hole to engage the pressure element at the hole such that a force is exerted by the pressure element onto the head that maintains the head at an adjustable angular position relative to the receiving part by friction.

Depending on the use or clinical application, it can be desirable to provide a bone anchoring device configured to restrict pivoting of the bone anchoring element with respect to the receiving part to a single plane, i.e., a uniplanar bone anchoring device, or to provide a monoaxial bone anchoring device in which the shank has a fixed angle, preferably a zero-angle, with respect to the receiving part.

Various designs of uniplanar bone anchoring devices are known, where the shank of the bone anchoring element can pivot in the receiving part only in a single plane. For example, U.S. Pat. No. 7,749,258 B2 describes a uniplanar bone anchoring device including a receiving part for receiving a rod, a pressure element, and a bone anchoring element being moveable relative to the receiving part in a limited angular range about the longitudinal axis of the receiving part, the angles lying in a single plane. The movement of the bone anchoring element relative to the receiving part is limited by a form-fit connection, including cooperating guiding surfaces at the head of the bone anchoring element and at the pressure element.

US 2004/0204711 A1 describes a bone screw having a head and a shank. The shank has a ball thereon, and the head has a socket for receiving the ball. The bone screw includes two set screws that engage the ball to lock the head in position relative to the shank.

A modular bone screw assembly is known from US 2017/0049482 A1, which includes a screw, a housing, a snap ring, a saddle, a set screw, and a rod. The bone screw assembly can allow for polyaxial or uniplanar movement of the screw relative to the housing.

SUMMARY

There is still a need to provide a bone anchoring device having a simple structure with only few parts, that may facilitate implementation of at least a polyaxial and/or a uniplanar and/or a monoaxial bone anchoring device. Thus, it is an objection underlying the invention to provide a bone anchoring device that can be used in a modular manner, enabling a selectable functionality in terms of a polyaxial, a monoaxial, or a uniplanar design.

According to an embodiment of the invention, a bone anchoring device for coupling a rod to bone is provided, the bone anchoring device including an anchoring element with a shank for anchoring in bone and a head, a receiving part having a first end and a second end, a channel for receiving the rod, a passage extending from the first end to the second end, the passage defining a central axis, and an accommodation space for accommodating the head of the bone anchoring element, and at least one through hole transverse to the central axis, the through hole forming an internal thread. The bone anchoring device further includes at least one restriction element configured to be inserted into the through hole of the receiving part, the restriction element including an external thread, and a pressure element configured to be arranged in the passage and to exert pressure onto the head when the head and the pressure element are in the receiving part, such that the head is pivotable with respect to the receiving part and can be locked at an angle relative to the receiving part. When the restriction element is in the through hole, the restriction element is configured to interact with the pressure element or with the head to prevent a pivoting motion of the head in the receiving part, or to restrict a pivoting motion of the head to a single plane.

Transverse to the central axis means that an axis of the transverse hole intersects the central axis, preferably where the axis of the transverse hole is substantially perpendicular to the central axis.

With the bone anchoring device according to embodiments of the invention, it is possible to selectively use the bone anchoring device as a polyaxial bone anchoring device or as a monoaxial bone anchoring device. The monoaxial bone anchoring device can be implemented by applying the restriction elements to prevent any pivoting or tilting motion of the head of the bone anchoring element relative to the receiving part. This can be carried out at any time before surgery. Thus, with only few parts, the inventory required for surgery can be reduced.

Moreover, it is possible to use a bone anchoring device that has been originally designed as a polyaxial bone anchoring device for various monoaxial applications, such as trauma applications, growing rod applications, posterior scoliosis correction, anterior scoliosis surgery, or anterior scoliosis tethering.

In a further development, the restriction elements includes a break-off portion so that after forming the monoaxial bone anchoring device, the break-off portion can be removed to reduce an outer dimension of the bone anchoring device.

In a still further embodiment, the receiving part of the bone anchoring device is a first receiving part. A second receiving part can be coupled via the through hole to the first receiving part using a coupling element. By means of this, two rods can be coupled in parallel to a single bone anchoring element.

In a still further embodiment, the head of the bone anchoring element defines recesses which can be engaged by restriction elements to prevent any pivoting of the bone anchoring element relative to the receiving part or to restrict a pivoting motion of the head in the receiving part to a single plane. The recesses are distinct from each other and preferably located at opposite sides of the head relative to the shank axis. Thus, by selecting a suitable restriction element, either a monoaxial or a uniplanar bone anchoring device can be provided. If the restriction elements are omitted, the bone anchoring device functions as a polyaxial bone anchoring device. By the modular design, the field of applications is considerably enlarged.

In a still further embodiment, a bone anchoring device for coupling a rod to bone includes an anchoring element for anchoring in bone and a head, a first receiving part having a first end and a second end, a channel for receiving a first rod, a passage extending from the first end to the second end, the passage defining a central axis, and an accommodation space for accommodating the head of the bone anchoring element, and at least one through hole transverse to the central axis, a pressure element configured to be arranged in the passage and to exert pressure onto the head when the head and the pressure element are in the first receiving part, such that the head is pivotable with respect to the receiving part and can be locked at an angle relative to the receiving part, and a second receiving part having a first end and a second end, a channel for receiving a second rod, a passage extending from the first end to a distance from the second end, the passage defining a central axis, and at least one through hole transverse to the central axis, and a connection element configured to be inserted into the through hole of the second receiving part and the through hole of the first receiving part to connect the second receiving part to the first receiving part.

With such embodiments of the invention, a bone anchoring device designed originally as a polyaxial bone anchoring device for a single rod can be easily transformed or converted to a polyaxial bone anchoring device having two receiving parts for receiving two rods. By applying a restriction element, the bone anchoring device according to embodiments of the invention can be transformed or converted to a monoaxial or a uniplanar bone anchoring device.

Since the receiving part may generally be more expensive and/or more difficult to manufacture compared to the bone anchoring element, the manufacturing costs and/or the costs for stock holding can be decreased if the same receiving part can be used for more than one clinical application.

BRIEF DESCRIPTION OF THE DRAWINGS

Further features and advantages will become apparent from the description of embodiments by means of the accompanying drawings. In the drawings:

FIG. 24 shows a first perspective view from above a second receiving part of the bone anchoring device of FIGS. 22 and 23.

FIG. 25 shows a second perspective view from above the second receiving part of FIG. 24.

FIG. 26 shows a top view of the second receiving part of FIGS. 24 and 25.

FIG. 27 shows a cross-sectional view of the second receiving part of FIGS. 24 to 26, the cross-section taken along line F-F of FIG. 26.

FIG. 28 shows a perspective view from above a connection element of the bone anchoring device of FIGS. 22 and 23.

FIG. 29 shows a perspective view from below the connection element of FIG. 28.

FIG. 30 shows a cross-sectional view of the connection element of FIGS. 28 and 29, the cross-section taken in a plane including a screw axis of the connection element.

FIG. 35 shows a perspective view from above the receiving part of the bone anchoring device of FIGS. 31 to 34.

FIG. 36 shows a perspective view from below the receiving part of FIG. 35.

FIG. 37 shows a cross-sectional view of the receiving part of FIGS. 35 and 36, the cross-section taken in a plane including the central axis of the receiving part and perpendicular to the longitudinal axis of the rod channel.

DETAILED DESCRIPTION

Figure 1:
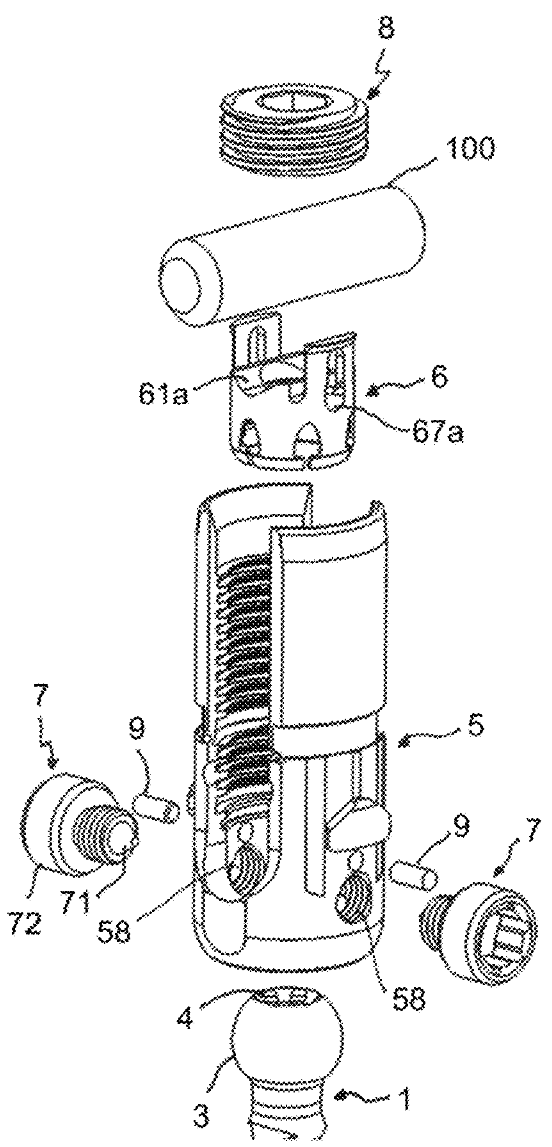
FIG. 1 shows a perspective exploded view of a bone anchoring device according to a first embodiment.

With reference to FIGS. 1 to 21, a first embodiment of a bone anchoring device is described. As shown in particular in FIGS. 1 to 3, the bone anchoring device includes a bone anchoring element 1 having a shank 2 for anchoring in bone or in a vertebra, and a head 3. The shank 2 has a bone engagement feature, such as a thread. The head 3 is shaped as a segment of a sphere, thus having a spherically-shaped outer surface portion. The spherically-shaped outer surface portion is preferably smooth, e.g., is thread-free and/or free from corrugations. In addition, the head 3 has at its free end an engagement portion 4 for engagement with a tool, such as a driver. Further, the bone anchoring device includes a receiving part 5 for receiving the head 3 of the bone anchoring element 1 and for receiving a rod 100 which is configured to connect several bone anchoring devices. In the receiving part 5, a pressure element 6 is provided for exerting pressure onto the head 3 of the bone anchoring element 1 and for providing support for the rod 100. A pair of restriction elements 7 are configured to cooperate with the pressure element 6 to cause the pressure element 6 to exert a force on an inserted head 3, such that the head 3 is prevented or restricted from pivoting with respect to the receiving part 5. To lock the head 3 and the rod 100 in the receiving part 5, a locking element 8 in the form of an inner screw or set screw is provided.

Referring in addition to FIGS. 4 to 7, the receiving part will be explained in greater detail. The receiving part 5 has a first or top end 5*a* and a second or bottom end 5*b* opposite to the top end 5*a*. In general, the receiving part 5 may have a substantially cylindrical outer shape, with a central longitudinal axis C extending through the top end 5*a* and the bottom end 5*b*. Coaxial with the central axis C, a passage 51 is provided that extends from the top end 5*a* to the bottom end 5*b*, and that forms an opening 52 at the bottom end 5*b*. At a distance from the top end 5*a*, the passage 51 widens into an accommodation space 53 that is configured to receive the head 3 and at least a portion of the pressure element 6 therein. Adjacent to the opening 52 at the bottom end 5*b*, the accommodation space 53 narrows towards the opening 52, forming a narrowing portion 53*a*, which may be, for example, a tapered, and more particularly a conical, surface that may cooperate with a corresponding surface of the pressure element 6. The width of the opening 52 may be greater than the greatest width of the head 3, so that the head 3 may be inserted from the bottom end 5*b* into the accommodation space 53. To enable the insertion of the head 3 from the bottom end 5*b*, the width of the accommodation space 53 is such that the pressure element 6 can expand therein to permit insertion of the head 3.

The receiving part 5 further has a substantially U-shaped recess 54 starting at the top end 5*a* and extending in a direction of the bottom end 5*b*. By means of the U-shaped recess 54, two free legs 55 are formed and define a channel that is open towards the first end 5*a* for receiving the rod 100.

On an inner surface of the legs 55, an inner thread 56 is formed, which is in the exemplary embodiment a square thread or another flat thread. A circumferential first groove 57*a* may be provided at an inner wall of the legs 55, at a distance from a bottom 54*a* of the U-shaped recess 54. The first inner groove 57*a* may provide a stop for restricting an upward movement of the pressure element 6 towards the first end 5*a* when the pressure element 6 is assembled with the receiving part 5 at an insertion position. Between the circumferential first groove 57*a* and the accommodation space 53, there may be a circumferential second groove 57*b* for engagement with a portion of the pressure element 6 to secure a pre-locking position of the pressure element 6.

The receiving part 5 further includes two threaded through holes 58 extending from an outer surface of the receiving part 5 into the passage 51. The threaded through holes 58 may be arranged at 180° offset from each other and at 90° relative to the channel formed by the U-shaped recess 54. The axes a of the threaded through holes 58 extend preferably substantially perpendicular, more preferably perpendicular, to the central axis C and intersect the central axis C. An axial position of the axes a of the threaded through holes 58, i.e., a distance from the bottom end 5*b*, is such that, when the pressure element 6 and the head 3 are inserted, the restriction elements 7 that extend through the threaded through holes 58 can engage the pressure element 6. More specifically, the position of the threaded through holes 58 is such that, a force is exerted by the restriction elements 7 via the pressure element 6 onto the inserted head 3 that prevents or restricts the head 3 from pivoting in the receiving part 5. In the embodiment, the axes a of the threaded through holes 58 are approximately at the axial position of the upper surface of an inserted head 3.

Figure 2:
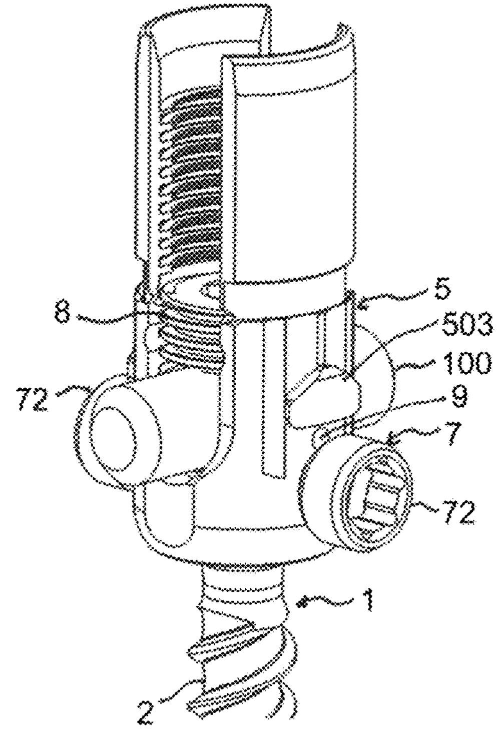
FIG. 2 shows a perspective view of the bone anchoring device of FIG. 1 in an assembled state.
Figure 3:
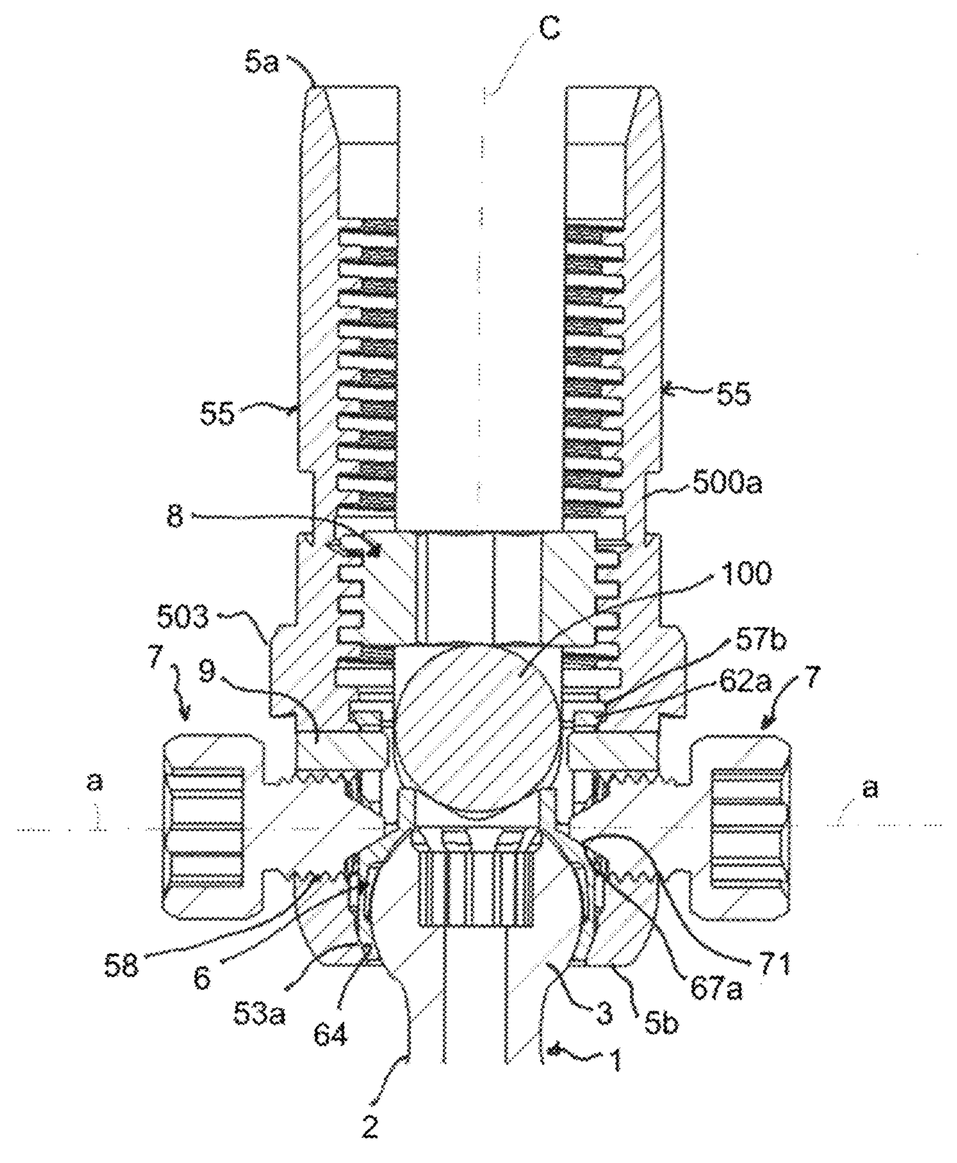
FIG. 3 shows a cross-sectional view of the bone anchoring device of FIGS. 1 and 2, the cross-section taken in a plane including a central axis of a receiving part of the bone anchoring device and perpendicular to a rod axis of an inserted rod.
Figures 4, 5, 6, 7:
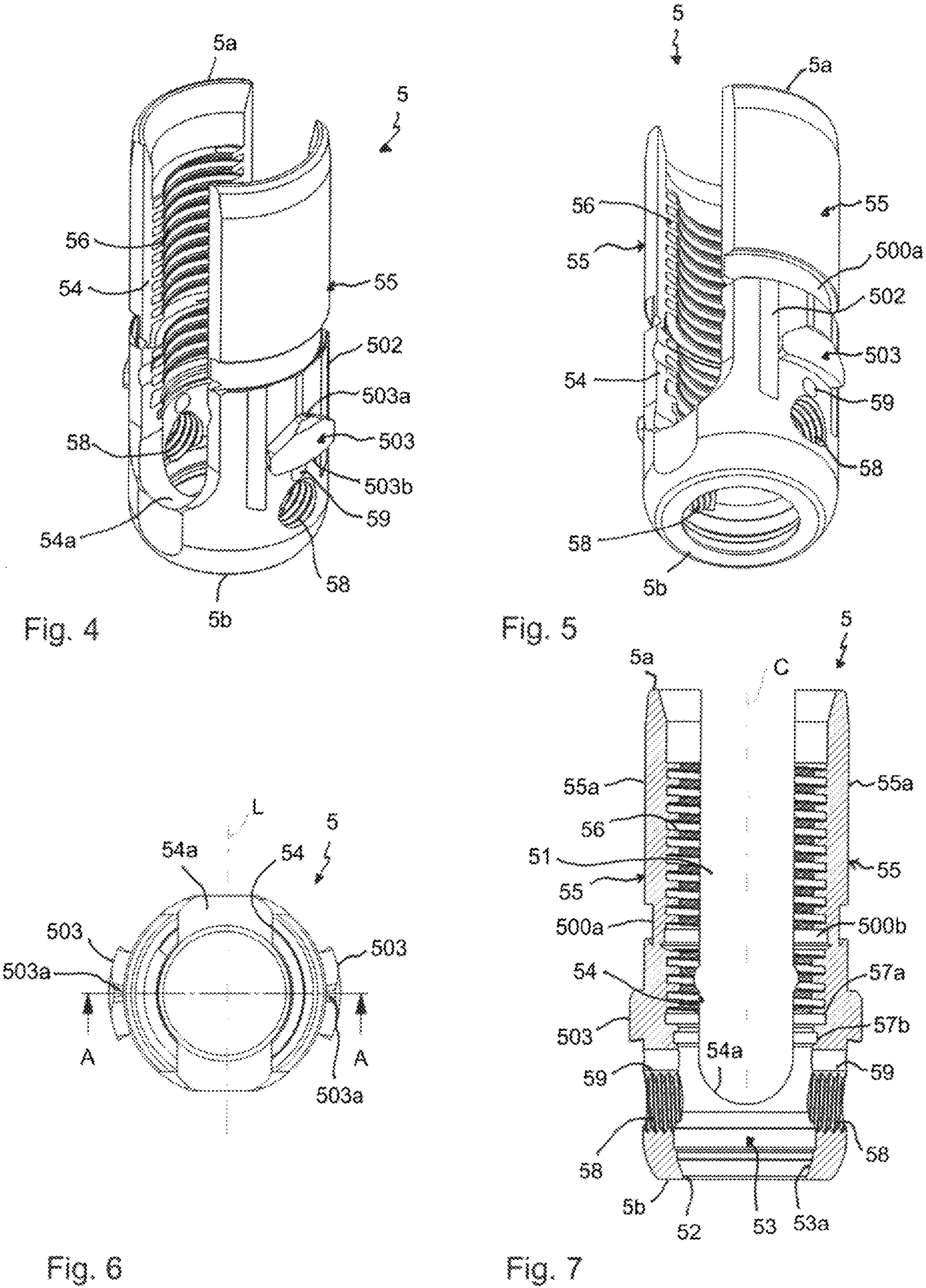
FIG. 4 shows a perspective view from the receiving part of the bone anchoring device of FIGS. 1 to 3.
FIG. 5 shows a perspective view from below the receiving part of FIG. 4.
FIG. 6 shows a top view of the receiving part of FIGS. 4 and 5.
FIG. 7 shows a cross-sectional view of the receiving part of FIGS. 4 to 6, the cross-section taken along line A-A in FIG. 6.
Figure 8:
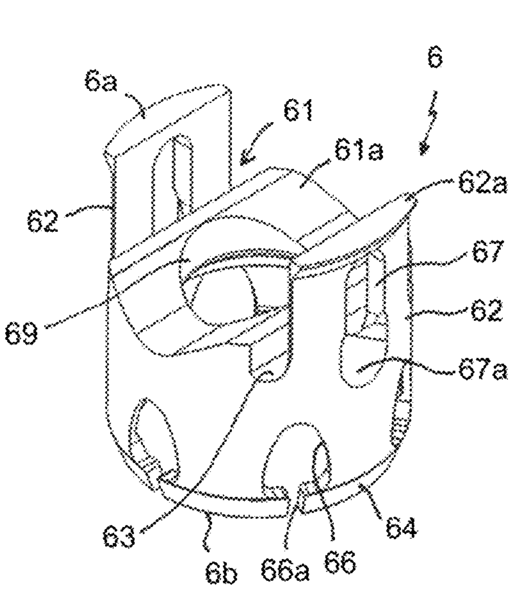
FIG. 8 shows a perspective view from above a pressure element of the bone anchoring device of FIGS. 1 to 3.
Figure 9:
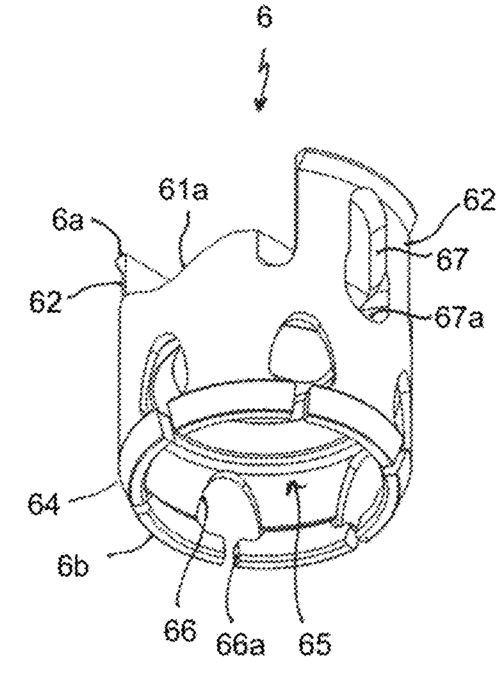
FIG. 9 shows a perspective view from below the pressure element of FIG. 8.
Figure 10:
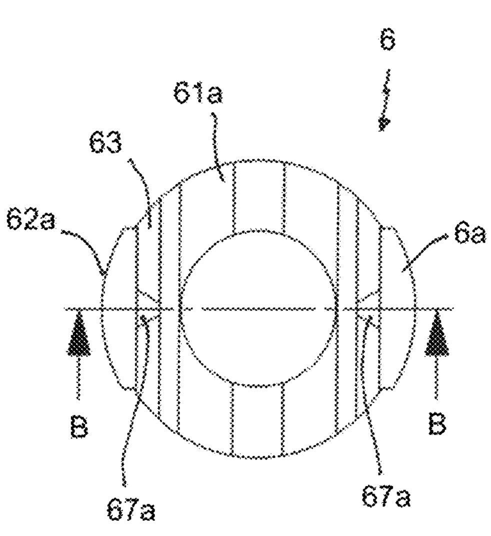
FIG. 10 shows a top view of the pressure element of FIGS. 8 and 9.
Figure 10:
Figure 11:
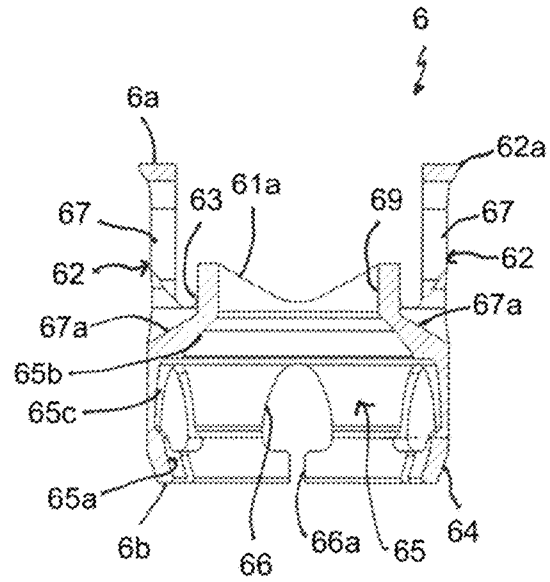
FIG. 11 shows a cross-sectional view of the pressure element of FIGS. 8 to 10, the cross-section taken along line B-B in FIG. 10.

In addition, transverse holes 59, preferably with a smaller diameter than the threaded through holes 58, may extend through the legs 55, respectively, in a direction perpendicular to the central axis C and at a circumferential position approximately at the center of each of the legs 55, axially above the threaded through holes 58 in the direction towards the top end 5*a*. The through holes 59 may serve for accommodating pins 9, as shown in FIGS. 1 to 3. The pins 9 are configured to engage the pressure element 6 to form a securing device to secure the pressure element 6 against rotation. In addition, the pins 9 may limit an upward movement of the pressure element 6.

At a distance from the bottom end 5*b* and above the bottom 54*a* of the U-shaped recess 54, a circumferential groove 500*a* may be provided in the outer surface of each of the legs 55. At a corresponding position on the inner surface of the legs 55, a circumferential groove 500*b* may be provided so that at the position of the outer groove 500*a*, the legs 55 are weakened. As a result, an upper portion 55*a* of the legs 55, respectively, up to the top end 5*a*, may be broken off. Thus, the upper portion 55*a* of the legs 55, respectively, serve as extended tabs that facilitate easier guiding of instruments or the fixation screw 8 downwards into the receiving part. This is particularly useful in minimally-invasive surgery (MIS), where only small incisions are made in a patient's skin.

At the outside of the legs 55, for example, longitudinal recesses 502 and/or attachment projections 503 may be provided for engagement with a tool or an instrument. The attachment projections 503 may be located above the threaded through holes 58 and the transverse holes 59 in a direction towards the top end 5*a* but below the grooves 500*a*.

In greater detail, the attachment projection 503 may have, in a plane view onto the projection 503, a substantially triangular shape with a tip 503*a* facing towards the top end 5*a*. A circumferential width of the attachment projection 503 at the base 503*b* opposite to the tip 503*a* may be the same as or greater than a width of the threaded through holes 58.

Referring further to FIGS. 8 to 11, the pressure element 6 is described. Preferably, the pressure element 6 is a monolithic piece which is configured to be arranged in the passage 51 and to encompass the head 3 laterally and from a free end of the head to exert pressure onto the head when the head 3 and the pressure element 6 are in the receiving part 5, such that the head is pivotable with respect to the receiving part and can be locked at an angle relative to the receiving part.

In greater detail, the pressure element 6 has a first or top end 6*a* and a second or bottom end 6*b*, and may be substantially cylindrical with an outer diameter that allows the pressure element 6 to move in the passage 51 of the receiving part 5. At the top end 6*a*, a rod receiving recess 61 is formed, with a rod support surface 61*a*. The rod support surface 61*a* may have a substantially V-shaped cross-section with a longitudinal axis L (see, e.g., FIG. 6) extending substantially perpendicular to a cylinder axis of the pressure element 6, the latter of which is configured to coincide or be coaxial with the central axis C of the receiving part 5 when the pressure element 6 is in the receiving part 5. The depth of the rod receiving recess 61 may be smaller than a diameter of the rod 100. Hence, when the rod 100 rests on the rod support surface 61*a*, the rod projects over and past the top end 6*a* of the pressure element as shown, for example, in FIG. 3. The V-shape of the rod support surface 61*a* more easily facilitates use of rods with different diameters.

Moreover, the rod receiving recess 61 is shaped such that two free legs 62 are formed that may be separated from the rod support surface 61*a* on each side by a groove 63. By means of this, the legs 62 are slightly flexible in a direction transverse to the longitudinal axis of the rod support surface 61. A free end of the legs 62 may have a radially protruding rim 62*a*, an upper surface of which forms the top end 6*a* of the pressure element 6. The rim 62*a* is configured to engage the grooves 57*a*, 57*b* provided at the inner surface of the legs 55 of the receiving part 5, to secure the insertion position or the pre-locking position of the pressure element 6 in the receiving part 5.

Adjacent to the bottom end 6*b* of the pressure element 6, an outer surface portion 64 may be tapered, preferably conically-shaped, and may be configured to cooperate with the narrowing portion 53*a* of the receiving part 5. Further, a hollow head receiving portion 65 is formed in the pressure element 6, with an opening at the bottom end 6*b* for inserting the head 3. The head receiving portion 65 may have lower and upper substantially spherical sections 65*a*, 65*b*, respectively, that are shaped so as to matingly receive the spherical head 3. An intermediate section 65*c* has a greater inner diameter for facilitating the insertion of the head 3. In addition, a plurality of recesses 66 are formed that extend completely radially through the pressure element 6 into the widened section 65*c* and which are open to the second end via substantially axially extending slits 66*a*. The recesses 66 may have an inverted drop shape, with the broader portion located closer to the bottom end 6*b*. The recesses 66 and the slits 66*a* are configured to spread or enlarge when the head 3 is inserted. In general, the number, shape and size of the recesses 66 are selected such that a desired flexibility is achieved that allows insertion of the head 3 through the bottom end of the pressure element until the head 3 is received in the head receiving portion 65. The size of the head receiving portion 65 may also be such that the head 3 can be held therein by friction before a final locking is effected.

At the center of each of the legs 62 in a circumferential direction, an axially extending elongate through hole 67 is provided, that serves for receiving the pins 9 and the restriction elements 7, as shown in FIGS. 1 to 3. For receiving a portion of the restriction elements 7, the bottom of the elongate through hole 67 has a broadened portion with a substantially conical shape that forms a first cooperating surface 67*a* that is configured to cooperate with a second cooperating surface at the restriction element 7, as described in greater detail below. The first cooperating surface 67*a* extends transversely to the central axis C, at an axial position below the groove 63 and slightly above the upper spherical portion 65*b* of the head receiving portion 65, as can be seen in particular in FIG. 11. This permits the restriction elements 7 to exert a force onto an upper portion of an inserted head 3 via the cooperating surfaces of the pressure element 6 and the restriction element 7. Lastly, a coaxial bore 69 is formed in the pressure element 6 for permitting access with a driver to the engagement recess 4 of the head 3.

Figure 12:
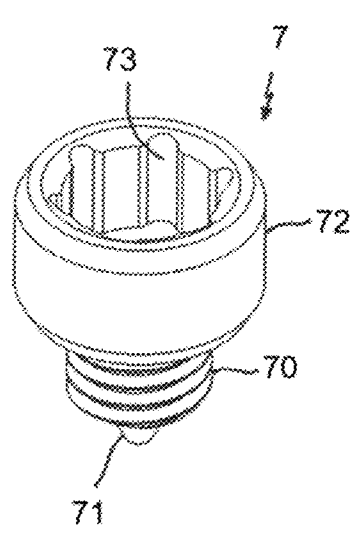
FIG. 12 shows a perspective view from above a restriction element of the bone anchoring device of FIGS. 1 to 3.
Figure 13:
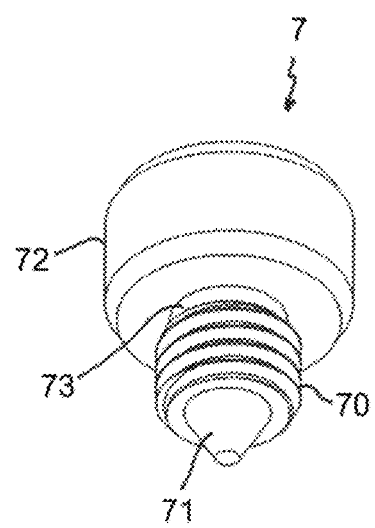
FIG. 13 shows a perspective view from below the restriction element of FIG. 12.
Figure 14:
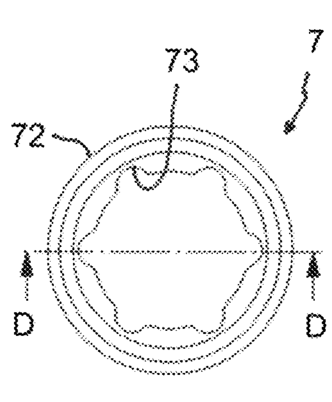
FIG. 14 shows a top view of the restriction element of FIGS. 12 and 13.
Figure 15:
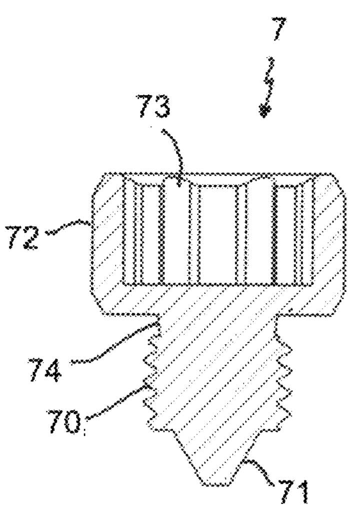
FIG. 15 shows a cross-sectional view of the restriction element of FIGS. 12 to 14, the cross-section taken along line D-D in FIG. 14.

Referring now to FIGS. 12 to 15, the restriction element 7 is described. The restriction element 7 includes a threaded portion 70 that is configured to cooperate with the threaded through hole 58 of the receiving part 5. A front portion 71 is formed as a cone that projects from the threaded portion 70 and that may have a flat end portion. An outer diameter of the base of the front portion 71 adjacent to the threaded portion 70 is smaller than an outer diameter of the threaded portion 70. In greater detail, the front portion 71 has a shape such that it fits into the lower conical portion of the elongate hole 67 of the pressure element 6. Thus, an outer surface of the conical front portion 71 forms the second cooperating surface that is configured to cooperate with the first cooperating surface 67*a* of the pressure element 6. A rear portion 72 on the other side of the threaded portion 70 opposite to the front portion 71 forms a head of the restriction element 7. The rear portion 72 is substantially cylindrical and has a greater outer diameter than the threaded portion 70. In the free end surface of the rear portion, an engagement recess 73 for engagement with a tool, such as a driver, is provided. The engagement recess 73 may have a torx-shape, as depicted in FIGS. 12 and 14. The overall size of the rear portion 72 is such that it can be easily gripped, so that the restriction element 7 can be screwed into the threaded hole 58 of the receiving part 5. Between the threaded portion 70 and the rear portion 72, a predetermined breaking area 74, i.e., a weakened section, is formed that has a slightly smaller outer diameter than the threaded portion 70. The rear portion 72 is configured to be broken off at the predetermined breaking area 74 when a torque is applied to the rear portion 72 that exceeds a predetermined torque.

The parts and portions of the bone anchoring device may be made of any material, preferably, however, of titanium or stainless steel, or of any bio-compatible metal or metal alloy or plastic material. For bio-compatible alloys, a NiTi alloy, for example, Nitinol, may be used. Other materials that can be used are, for example, magnesium or magnesium alloys. Bio-compatible plastic materials that can be used may be, for example, polyether ether ketone (PEEK) or poly-L-lactide acid (PLLA). The parts can be made of the same or of different materials from one another.

In use, the bone anchoring device can be applied as a polyaxial bone anchoring device or as a monoaxial bone anchoring device.

Figure 16:
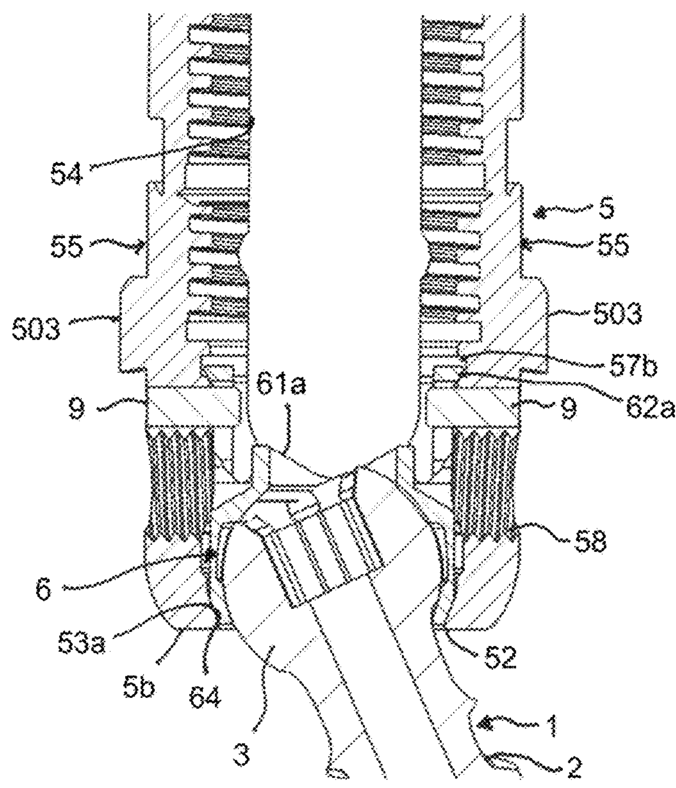
FIG. 16 shows a cross-sectional view of the bone anchoring device of FIGS. 1 to 3, without the restriction element and with the head being pivotable in the receiving part.

As shown in FIG. 16, the pressure element 6 is pre-assembled with the receiving part 5 such that the upper rim 62*a* of the pressure element 6 extends into the second groove 57*b* and the rod support surface 61*a* is aligned with the channel formed by the U-shaped recess 54. The pins 9 extend through the through holes 59 into the elongate recesses 67. Thereby, the pressure element 6 is secured against rotation. The head 3 of the bone anchoring element 1 may have been previously inserted from the bottom end 5*b* into the head receiving portion 65 of the pressure element. When the outer rim 62*a* is held into the second groove 57*b*, the pressure element 6 is in the pre-locking position, in which the narrowing outer surface portion 64 at the lower end of the pressure element 6 engages the narrowing inner surface portion 53*a* of the receiving part 5, so that the head 3 cannot be removed through the lower opening 52. In this position, the head 3 is still pivotable in the receiving part 5 as shown in FIG. 16. When the bone anchoring device is used as a polyaxial bone anchoring device, the rod 100 is inserted into the U-shaped recess until it rests on the rod support surface 61*a* of the pressure element 6. To lock the bone anchoring device, i.e., to lock the head 3 and the rod 100 in the receiving part 5, the locking element 8 is screwed between the legs 55 until it presses onto the rod, so that the pressure element is moved further downward until it locks the head 3 at a particular angular position with respect to the receiving part 5.

Figure 17:
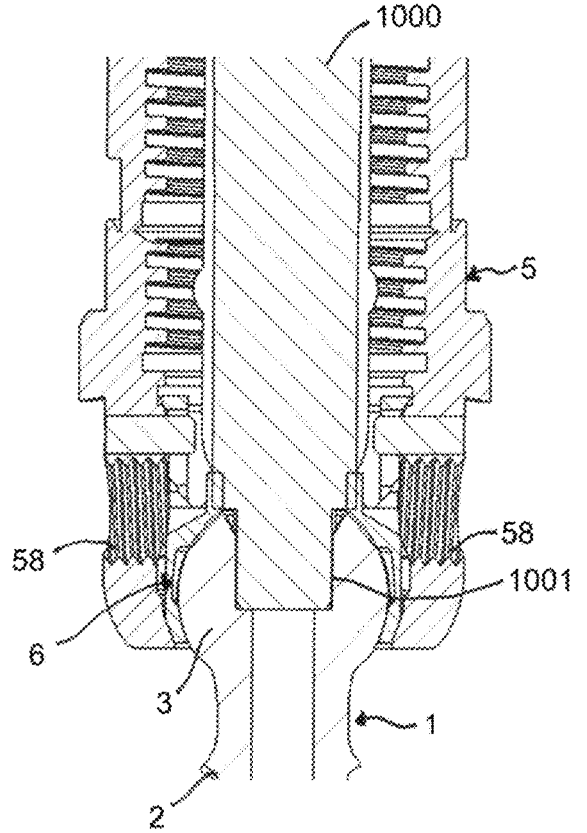
FIG. 17 shows the cross-sectional view of FIG. 16, with an instrument inserted into the receiving part and into a head of a bone anchoring element of the bone anchoring device to hold the bone anchoring element at a zero-angle position with respect to the receiving part.

When the bone anchoring device is intended to be used as a monoaxial bone anchoring device, i.e., when the axis of the shank 2 is permanently coaxial with the central axis C of the receiving part 5, the restriction elements 7 can be used. First, as shown in FIG. 17, an instrument 1000 that includes an elongate bar with a front portion 1001 is inserted into the receiving part 5 from the top end 5*a* until the front portion 1001 engages the tool engagement recess 4 of the head 3. By means of this engagement, the bone anchoring element 1 assumes a zero-angle position relative to the receiving part 5, i.e., the shank axis of the shank 2 is coaxial with the central axis C.

Figure 18:
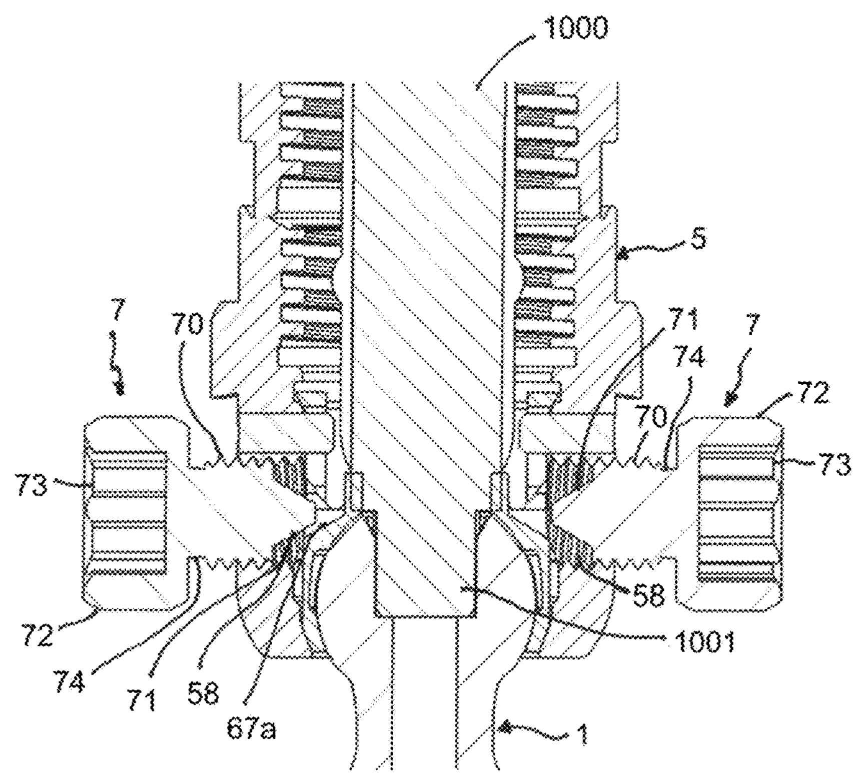
FIG. 18 shows the cross-sectional view of FIG. 17, with the restriction elements prior to full insertion.
Figure 19:
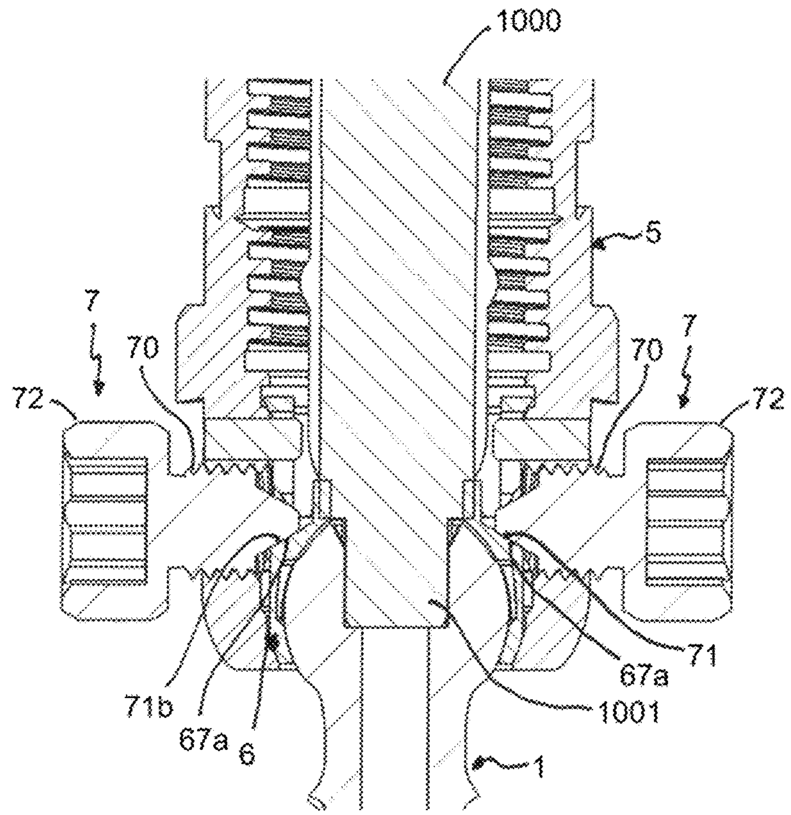
FIG. 19 shows the cross-sectional view of FIG. 18, with the restriction elements at an end position.

Next, as depicted in FIG. 18, the restriction elements 7 are screwed into the threaded holes 58, respectively, until the conical front portion 71 with the second cooperating surface engages the first cooperating surface 67*a* in the lower portion of the elongate hole 67 of the pressure element 6, as depicted in FIG. 19. By means of this, an increasing pressure is exerted via the pressure element 6 onto the head 3 until the bone anchoring element 1 is locked at the zero-angle position. The position of the longitudinal axes a of the threaded through holes 58 is selected such that the force generated by the restriction elements 7 achieve a full or almost full locking of the head 3 in the receiving part 5. Also, the bone anchoring element 1 is prevented from rotation when the restriction elements 7 are fully tightened.

Figure 20:
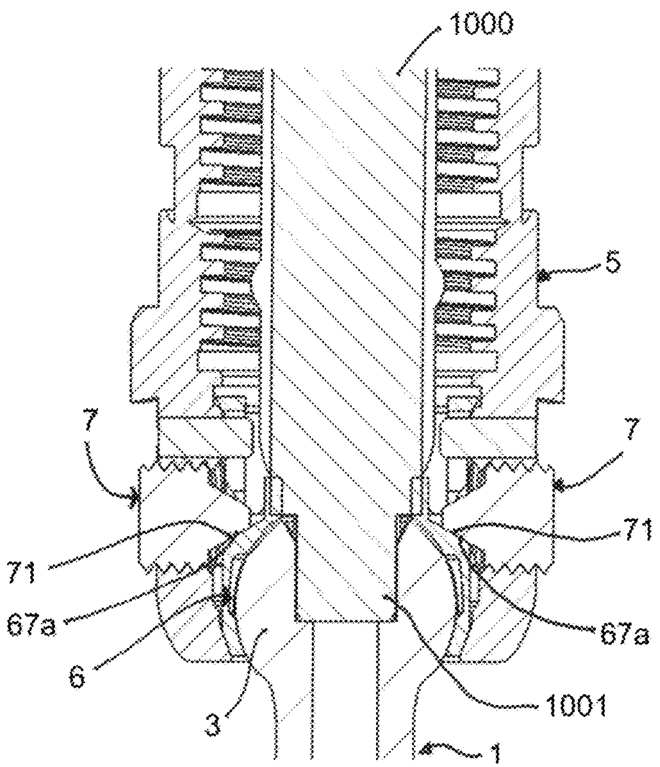
FIG. 20 shows the cross-sectional view of FIG. 19, with the restriction elements at the end position, and with break-off portions of the restriction elements broken off.
Figure 21:
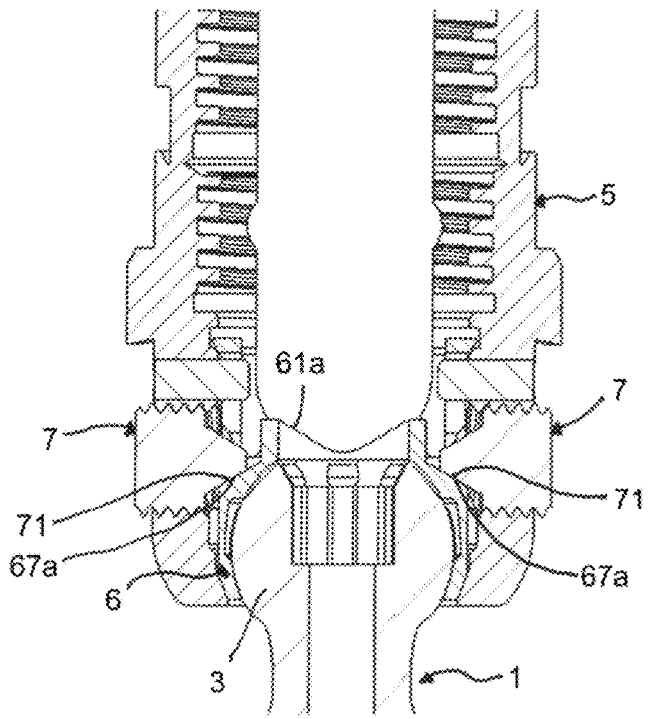
FIG. 21 shows the cross-sectional view of FIG. 20, with the instrument being removed.

When the counterforce exerted by the first cooperating surface 67*a* onto the second cooperating surface 71 of the restriction element 7 exceeds a predefined value, the rear portion 72 can be broken off from the threaded portion 70 at the predetermined breaking area 74 when a further torque is applied on the restriction element 7, as depicted in FIG. 20. Since the head 3 of the bone anchoring element 1 is locked at a zero-angle position, the instrument 1000 can be subsequently removed, as shown in FIG. 21. Hence, in FIG. 21, a monoaxial bone anchoring device is shown that can be used like any other monoaxial bone anchoring device. By engagement of the tool recess 4 of the head with a driver that extends through the bore 69 in the pressure element, the monoaxial bone anchoring device can be inserted into a bone part or a vertebra.

It shall be noted that the break-off portions 55*a* of the legs 55 can be broken off after final locking of the bone anchoring device with the locking element 8.

Figure 22:
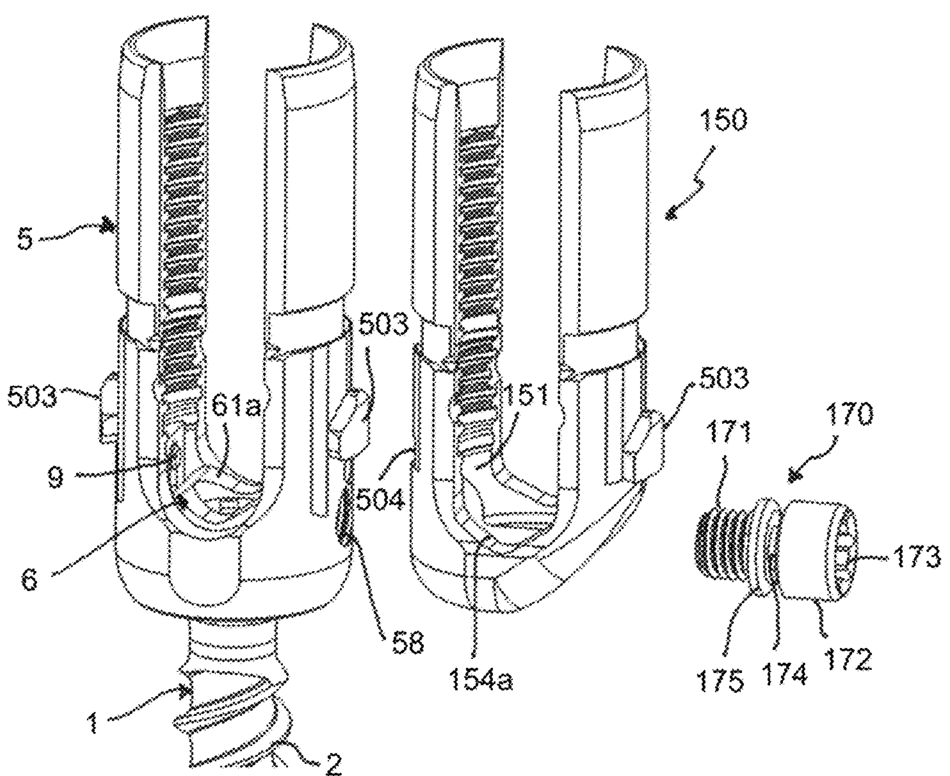
FIG. 22 shows a perspective exploded view of a bone anchoring device according to a second embodiment.
Figure 23:
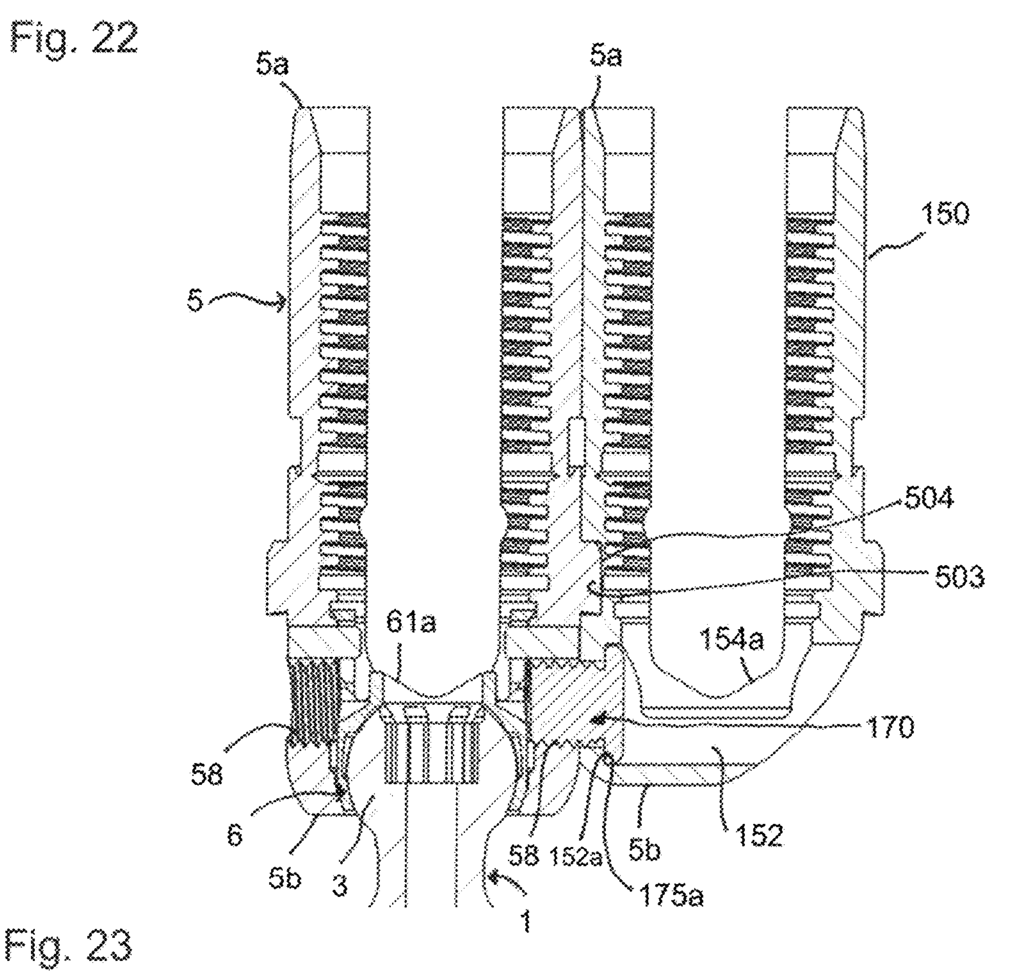
FIG. 23 shows a cross-sectional view of the bone anchoring device of FIG. 22 in an assembled state, the cross-section taken in a plane including central axes of receiving parts of the bone anchoring device and being perpendicular to longitudinal axes of rod channels of the receiving parts.

Referring to FIGS. 22 to 30, a second embodiment of the bone anchoring device is described. Parts and portions that are identical or similar to the first embodiment are marked with the same reference numerals, and the descriptions thereof will not be repeated. As can be seen in FIGS. 22 and 23, the bone anchoring device according to the second embodiment includes the bone anchoring device according to the first embodiment, i.e., the receiving part 5 with the pressure element 6 and the bone anchoring element 1. In the second embodiment, the receiving part 5 is a first receiving part. In addition, the bone anchoring device includes a second receiving part 150 and a connection element 170. The connection element 170 is configured to connect the second receiving part 150 to the first receiving part 5 using one of the threaded through holes 58 in the first receiving part 5. By means of this arrangement, two rods can be connected to a single bone anchoring element 1. Such an application may be used, for example, in a growing rod application, in which, for example, one rod is fixed and the other rod is slidable. This may be particularly useful in the treatment of scoliosis.

The second receiving part 150 differs from the first receiving part 5 in various aspects, but mainly in that the lower portion lacks a head receiving portion, and instead includes features for connecting the second receiving part 150 to the first receiving part 5. The second receiving part 150 is substantially cylindrical and defines a passage 151 that ends at a distance from the bottom end **5*b*. The bottom end 5*b* includes a substantially flat surface. A transverse bore 152 is formed above the bottom end 5*b* and at an axial position below a triangular-shaped attachment projection 503. An inner diameter of the transverse bore is greater than an outer diameter of a rear portion 172 of the connection element 170 (see FIGS. 22 and 23), such that the connection element 170 can be introduced and guided in the transverse bore 152. The transverse bore 152 is open to a side where the triangular projection 503 is located. A portion of the receiving part 150 around the transverse bore 152 is cut away so that the outer surface from the bottom end 5*b* towards or facing the triangular projection 503 is rounded. On the opposite side, the transverse bore 152 has a section 153 with a smaller diameter, such that a shoulder 152*a* is formed between the transverse bore 152 and the section 153. The shoulder 152*a* forms an abutment for a portion of the connection element 170. A rod receiving recess 154 extends from the top end to a distance from the bottom end. The rod receiving recess 154 has a V-shaped bottom region 154*a* that more easily facilitates supporting of rods with different diameters. By means of the recess 154, two free legs 155 are formed that include an upper portion 155*a* above the outer groove 500*a* and the inner groove 500*b*, similar to the first embodiment. The upper portion 155*a* may be broken off. On the leg 155 opposite to the leg 155 with the triangular projection 503, a triangular-shaped recess 504 is formed that has a shape corresponding to the shape of the triangular projection 503 and which is located at a position complementary to the position of the triangular-shaped projection 503 of the first receiving part 5, so that the triangular projection 503 of the first receiving part 5 can be received in the triangular recess 504 of the second receiving part 150. Moreover, in the outer surface of the leg 155 that has the triangular-shaped recess 504, a shallow groove 505 is formed that extends parallel to the central axis C from the top end 5*a* to substantially the bottom end 5*b*. The shallow groove 505 has a substantially cylindrical shape, so as to more easily fit to the outer surface of the leg 55 of the first receiving part 5**.

Referring in particular to FIGS. 28 to 30, the connection element 170 has a threaded portion 171 that is configured to be threaded into the threaded through hole 58 of the first receiving part 5. The front end of the connection element 170 at the threaded portion may have a flat end surface **171*a*. A rear portion 172 may be shaped like on the restriction element 7 of the first embodiment, i.e., the rear portion 172 may have a cylindrical shape with a greater outer diameter than the outer diameter of the threaded portion 171, and may further have a tool engagement recess 173. Adjacent to the rear portion 172, a predetermined breaking area 174 is formed, and between the predetermined breaking area 174 and the threaded portion 171, a ring-shaped abutment portion 175 is provided. The abutment portion 175 has a flat abutment surface 175*a* that faces towards the front end 171*a* and that is configured to abut against the shoulder 152*a* of the second receiving part 150. An outer edge of the abutment portion 175 that faces towards the rear portion 172** may be rounded.

In use, as can best be seen in FIGS. 22 and 23, the second receiving part 150 can be attached to the first receiving part 5, so that the bone anchoring device can be modified to become a bone anchoring device configured to receive two rods. First, the first receiving part 5 and the second receiving part 150 are aligned in a way such that the two rod channels are oriented in parallel. Then, the projection 503 of the first receiving part 5 is inserted into the complementary groove 504 at the second receiving part 150. Subsequently, the connection element 170 is inserted into the transverse bore 152 until the threaded portion 171 extends through the section 153 of the transverse bore 152 into the threaded through hole 58 of the first receiving part 5. The connection element 170 is then tightened until the abutment surface **175*a* abuts against the shoulder 152*a*. When a predetermined torque is exceeded, the rear portion 172 of the connection element 170 is broken off at the predetermined breaking area and can be removed. The first receiving part 5 and the second receiving part 150 are thus fixedly connected. Finally, the bone anchoring element 1 can be inserted into a bone or a vertebra, and respective rods 100 can be inserted into the first receiving part 5 and into the second receiving part 150. Depending on the clinical application, either both rods can be fixed with a locking member 8, or only one of the rods can be fixed with a locking member 8 while the other rod can remain slidable in the respective receiving part. It shall be noted that the first receiving part 5 and the second receiving part 150 can each receive rods of different diameters due to the V-shape of the rod support surface 61*a* of the pressure element 6 and the bottom 154*a* of the rod receiving recess 154**.

In the embodiment shown in FIG. 23, the bone anchoring device is still polyaxial, i.e., the head 3 is pivotable in the first receiving part 5. However, by using a restriction element 7 as shown in the first embodiment, that is inserted into the transverse through hole 58 opposite to the transverse through hole 58 in which the connection element 170 has been inserted, a monoaxial bone anchoring device can also be provided.

Referring now to FIGS. 31 to 51, a third and a fourth embodiment of the bone anchoring device is described. The parts form a modular system, and can be combined in various manners to provide a polyaxial bone anchoring device, a monoaxial bone anchoring device, or a uniplanar or monoplanar bone anchoring device.

Figure 31:
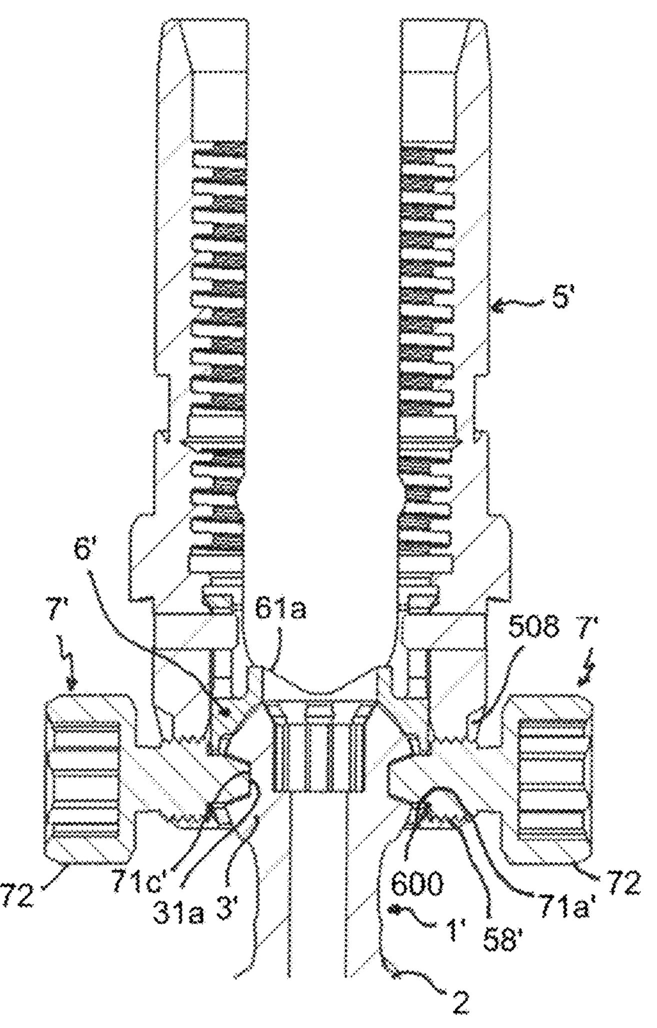
FIG. 31 shows a cross-sectional view of a bone anchoring device according to a third embodiment, the cross-section taken in a plane including a central axis of a receiving part of the bone anchoring device and being perpendicular to a longitudinal channel of a rod channel of the receiving part.
Figure 32:
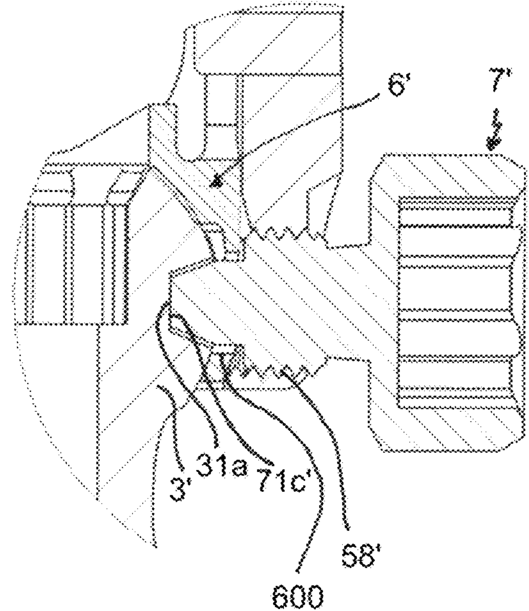
FIG. 32 shows an enlarged portion of a detail of FIG. 31.

First, with respect to FIGS. 31 to 45, the monoaxial bone anchoring device will be explained. The monoaxial bone anchoring device differs from the first embodiment according to FIGS. 1 to 21 in the design of the receiving part, the head of the bone anchoring element, and the restriction element. Referring specifically to FIGS. 31 to 37, the receiving part 5' differs from the receiving part 5 in the position and shape of the threaded through holes 58', which open into the accommodation space 53 at a lower position. All other portions are identical or similar to those of the receiving part 5 of the first embodiment, and the descriptions thereof are not repeated. The transverse threaded through holes 58' are located at an axial position at a distance from the bottom end 5*b* of the receiving part 5' that corresponds to a position where an inserted head 3' has its greatest outer diameter. As can be seen in FIGS. 31 and 32, the inserted restriction elements 7' engage the head 3' of the bone anchoring element 1 substantially at the region where the head 3' has its greatest outer diameter. Moreover, in the outer surface around the threaded through holes 58', a countersink 508 is formed that provides an abutment surface 508*a* for a restriction element of the fourth embodiment.

As shown in FIGS. 38 to 41, the pressure element 6' differs from the pressure element 6 of the first embodiment in that the pressure element 6' lacks the broadened lower portion of the elongate hole 67. Instead, the pressure element 6' has two through holes 600 that are located circumferentially 180° offset from each other and below the elongate hole 67. The through holes 600 are unthreaded and serve for allowing a portion of the restriction element 7' to extend therethrough. When the pressure element 6' is in the receiving part 5' and at the pre-locking position where the upper rim 62*a* is in the lower groove 57*b*, the through holes 600 are aligned with or at a same axial height as the threaded through holes 58' of the receiving part 5'.

Figure 42:
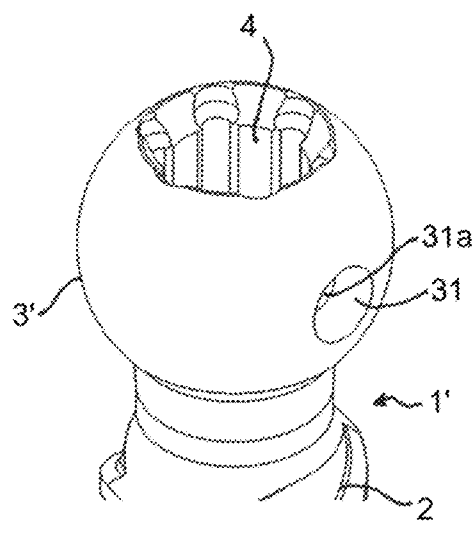
FIG. 42 shows a perspective view of a portion of a bone anchoring element of the bone anchoring device of FIGS. 31 to 34 (or of FIGS. 46 to 49 that follow).
Figure 43:
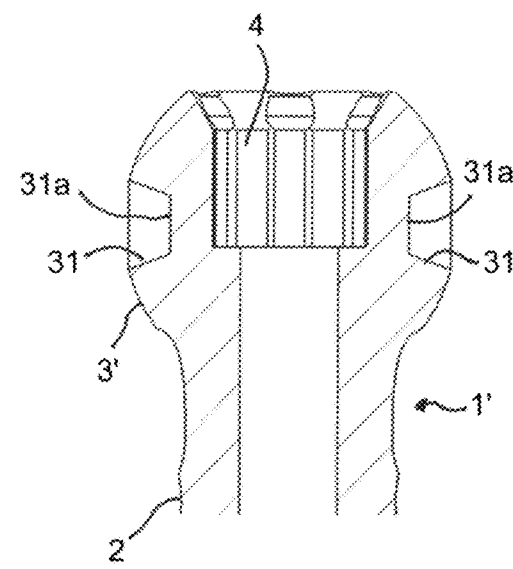
FIG. 43 shows a cross-sectional view of the bone anchoring element of FIG. 42.

Referring now to FIGS. 42 and 43, the bone anchoring element 1' will be explained. The bone anchoring element 1' differs from the bone anchoring element 1 of the first embodiment in the design of the head. The head 3' of the bone anchoring element 1' has, at an axial position corresponding to the greatest diameter of the head 3', two recesses 31 that are 180° offset from each other in a circumferential direction. The recesses 31 are conically shaped, corresponding to a front portion of the restriction element 7', and have a substantially flat bottom surface that forms a first cooperating surface 31*a* for cooperating with a second cooperating surface provided at the restriction element 7'. The dimension of the conical shape of the recesses 31 is such that a front portion of the restriction element 7' can be received therein, with some play in a direction parallel to the central axis C, when the bone anchoring device is assembled.

Optionally, the bone anchoring element 1', as well as the bone anchoring element 1, may have a coaxial channel for introducing substances, such as bone cement, to the bone.

Figure 44:
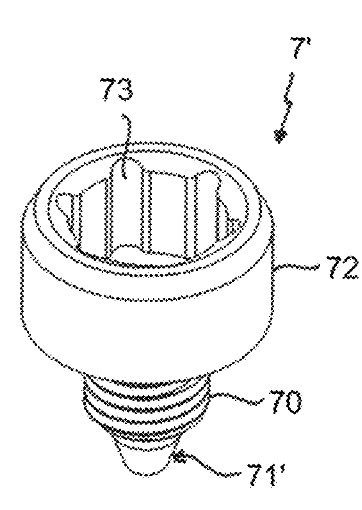
FIG. 44 shows a perspective view from above the restriction element of the bone anchoring device of FIGS. 31 to 34.
Figure 44:
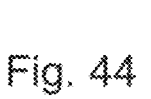
Figure 45:
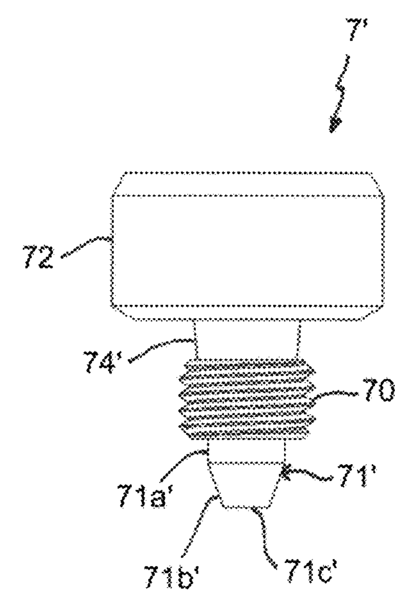
FIG. 45 shows a side view of the restriction element of FIG. 44.

Referring to FIGS. 44 and 45, the restriction element 7' is explained. The restriction element 7' differs from the restriction element 7 of the first embodiment mainly in the design of the front portion. The restriction element 7' includes the threaded portion 70 similar to the first embodiment, and an elongate front portion 71' that may have, adjacent to the threaded portion 70, a cylindrical portion 71*a'* with an outer diameter that is smaller than that of the threaded portion 70 and slightly smaller than the diameter of the hole 600 in the pressure element 6'. Adjacent to the cylindrical portion 71*a'*, there is a conical portion 71*b'* that narrows towards a flat end surface 71*c'*, that latter of which is configured to cooperate with the bottom 31*a* of the recesses 31 of the head 3'. Thus, the flat end surface 71*c'* forms a second cooperating surface. The rear portion 72 may be identical to the rear portion of the restriction element 7 of the first embodiment. The predetermined breaking area 74' between the rear portion 72 and the threaded portion 70 may widen conically from the threaded portion 70 towards the rear portion 72. However, any other shape for the predetermined breaking area may be contemplated.

When the receiving part 5' with the pre-assembled pressure element 6' and the anchoring element 1' is used without the restriction elements 7', the bone anchoring device functions as a polyaxial bone anchoring device. If the clinical application requires a monoaxial bone anchoring device, the restriction elements 7' are screwed into the threaded transverse holes 58' until the flat end surface 71*c'* presses against the flat bottom surface 31*a* of the recesses in the head 3' of the bone anchoring element 1'. By means of this, the shank 2 has a fixed orientation with respect to the receiving part 5', so that a monoaxial bone anchoring device is formed. Since the front portion 71' is sized to facilitate some axial play in the hole 600 of the pressure element, when finally locking the bone anchoring device using the locking element 8, the locking force of the fixation element 8 is transferred to the head 3' via the pressure element 6'.

Figures 33, 34:
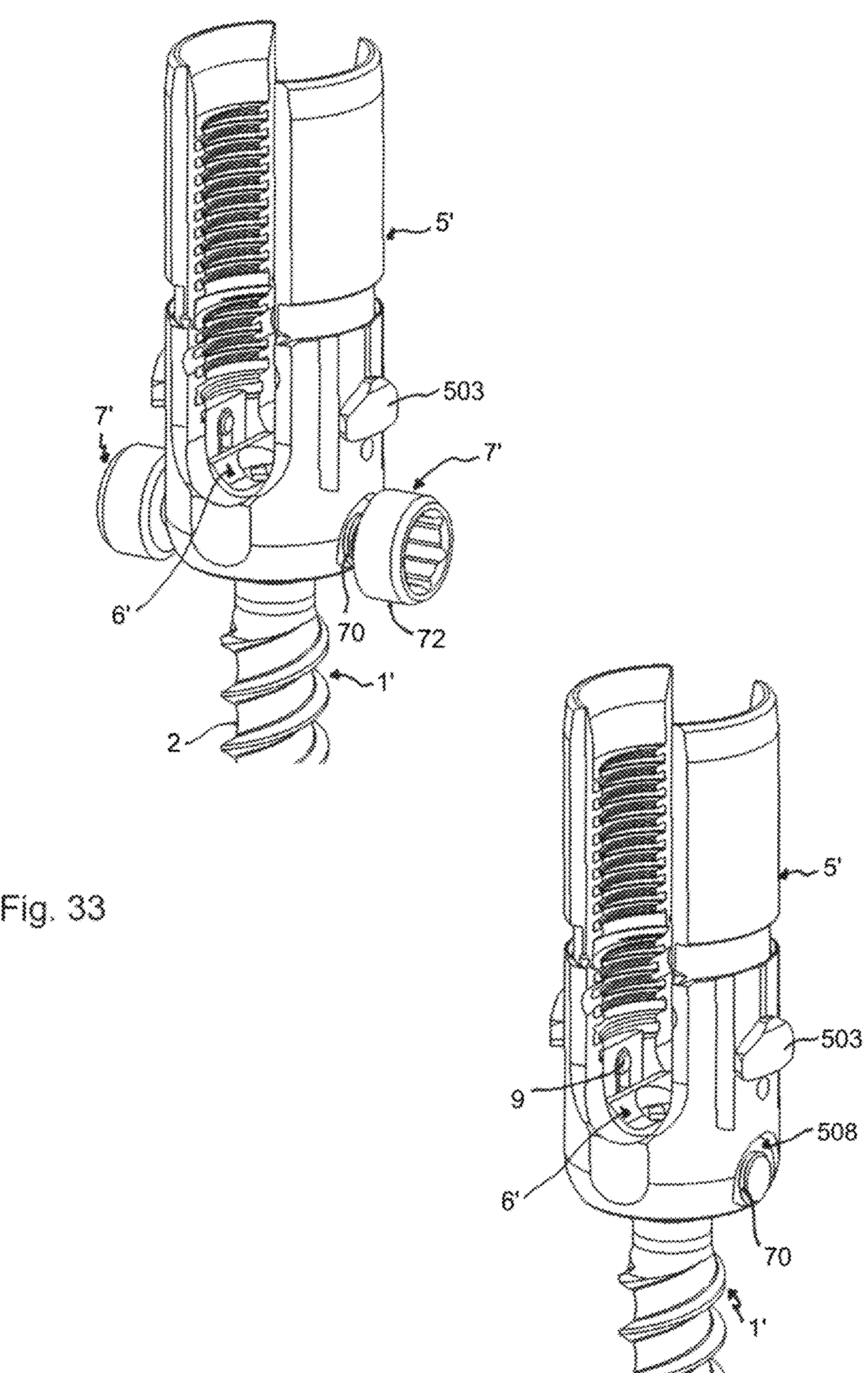
FIG. 33 shows a perspective view of the bone anchoring device of FIGS. 31 and 32, with inserted restriction elements.
FIG. 34 shows the perspective view of FIG. 33, with break-off portions of the restriction elements broken off.
Figure 38:
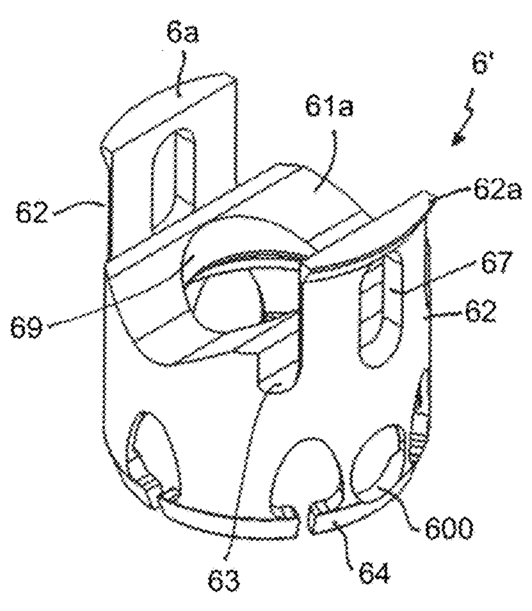
FIG. 38 shows a perspective view from above a pressure element of the bone anchoring device of FIGS. 31 to 34.
Figure 39:
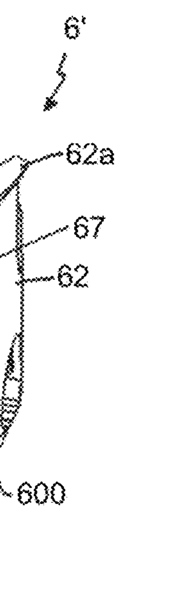
FIG. 39 shows a perspective view from below the pressure element of FIG. 38.
Figure 40:
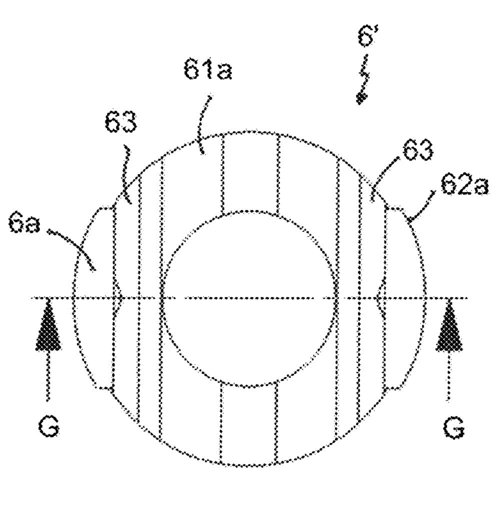
FIG. 40 shows a top view of the pressure element of FIGS. 38 and 39.
Figure 41:
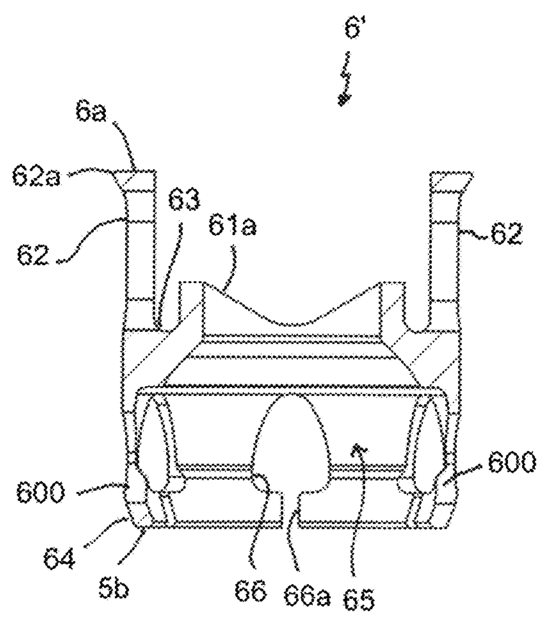
FIG. 41 shows a cross-sectional view of the pressure element of FIGS. 38 to 40, the cross-section taken along line G-G in FIG. 40.

When the torque applied to the rear portion 72 exceeds a predetermined torque, the rear portion 72 is broken off at the predetermined breaking area 74', as shown in FIG. 34.

Figure 46:
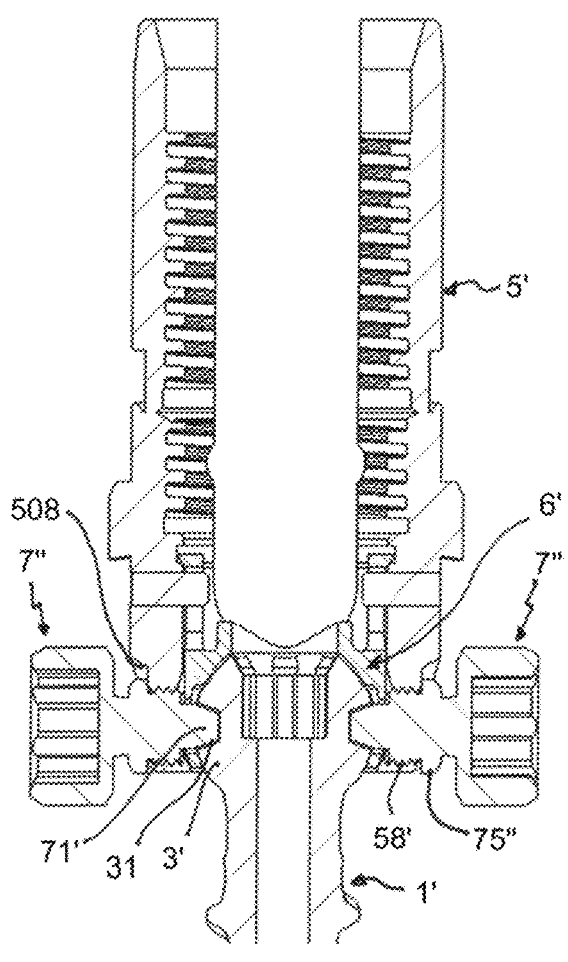
FIG. 46 shows a cross-sectional view of a bone anchoring device according to a fourth embodiment, the cross section taken in a plane including a central axis of a receiving part of the bone anchoring device and perpendicular to a longitudinal axis of a rod channel of the receiving part.
Figure 47:
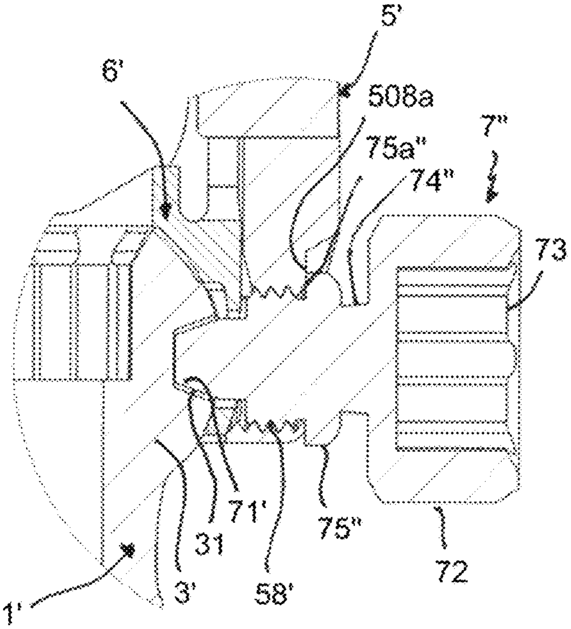
FIG. 47 shows an enlarged portion of a detail of FIG. 46.
Figure 48:
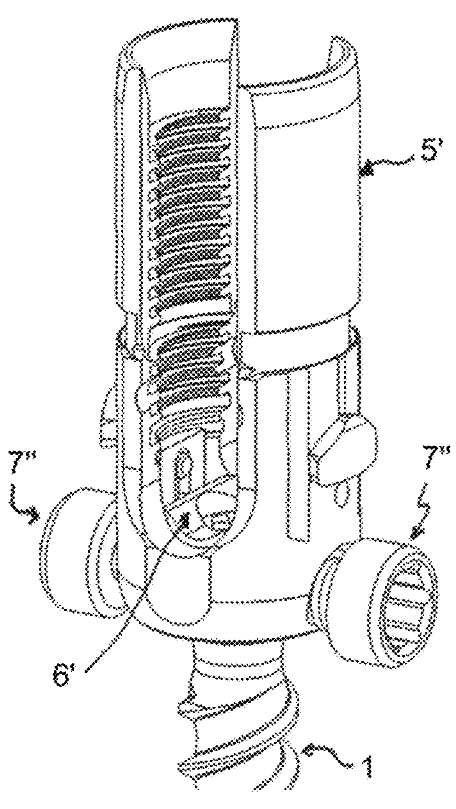
FIG. 48 shows a perspective view of the bone anchoring device of FIGS. 46 and 47, with inserted restriction elements.
Figure 49:
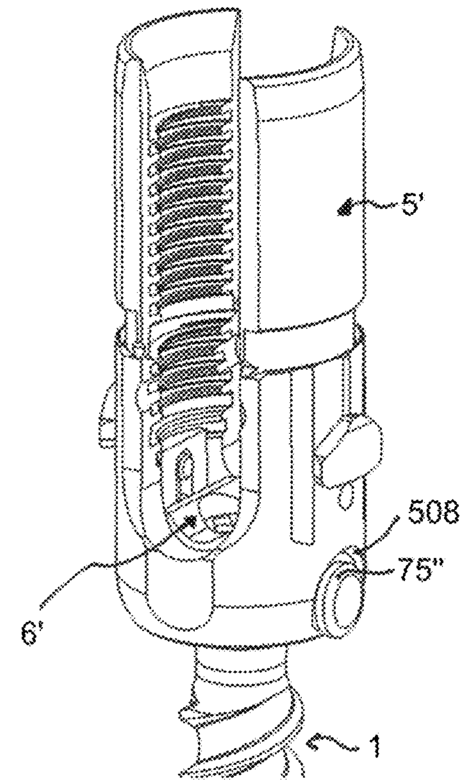
FIG. 49 shows the perspective view of FIG. 48, with break-off portions of the restriction elements broken off.
Figure 50:
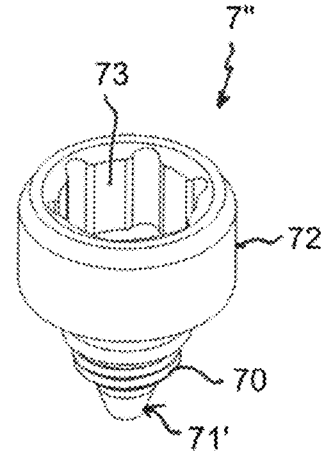
FIG. 50 shows a perspective view from above the restriction element of the bone anchoring device of FIGS. 46 to 49.
Figure 51:
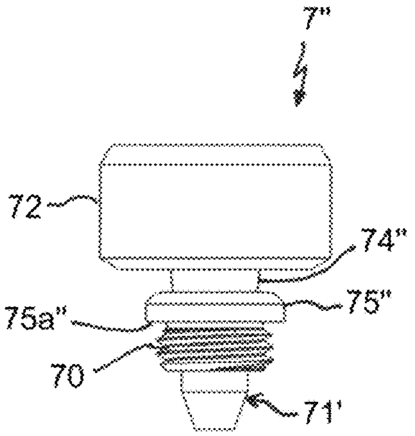
FIG. 51 shows a side view of the restriction element of FIG. 50.

Referring to FIGS. 46 to 51, the fourth embodiment of the bone anchoring device is described. The bone anchoring device of the fourth embodiment is identical to the bone anchoring device of the third embodiment, except for the design of the restriction elements. Hence, the receiving part 5', the pressure element 6', and the bone anchoring element 1' are identical to those of the third embodiment. The restriction elements 7", as shown in FIGS. 50 and 51, differ from the restriction elements 7' according to FIGS. 44 and 45 by the addition of an annular projection 75" that is formed adjacent to the threaded portion 70 on a side closer to the rear portion 72. The annular projection 75" has an outer diameter that is greater than the outer diameter of the threaded portion 70 and smaller than the outer diameter of the rear portion 72. On the side facing towards the free end surface 71*c'*, the annular projection 75" has a flat abutment surface 75*a"* that is configured to cooperate with the flat abutment surface 508*a* on the bottom of the countersink 508 around the threaded through holes 58' of the receiving part 5', which is shown in FIGS. 35 to 37. Hence, the flat abutment surface 75*a"* forms a second cooperating surface. The flat abutment surface 75*a"* is located at a distance with respect to the flat end surface 71*c'*, such that when the first cooperating surface 508*a* and the second cooperating surface 75*a"* are pressed against each other as shown in FIGS. 46 and 47, the conical front portion 71*b'* and the flat end surface 71*c'* do not press against the bottom 31*a* of the conical recess 31 in the head 3'. As a result, the bone anchoring element 1' can pivot around a pivot axis defined by the screw axis of the restriction elements 7". As a result, pivoting of the bone anchoring element 1' is restricted to a single plane. In the embodiment shown in FIGS. 46 to 49, the single plane is defined by a plane including the longitudinal axis of the rod channel and the central axis C of the receiving part 5'.

When a predetermined torque is exceeded, the rear portion 72 is broken off, so that a uniplanar bone anchoring device as shown in FIG. 49 is formed that can be inserted into the bone. Also in this embodiment, the axial play allows the pressure element 6' to move slightly downward when the bone anchoring device is finally locked by tightening the locking element 8. It shall be noted that, depending on the exact position of the abutment surface 75*a"* or the length of the front portion 71', a restriction element 7" may be provided which is configured to exert a pre-load on the head 3', where for example, the front surface 71*c'* slightly touches the bottom 31*a* of the recess 31, so that a specific angular position in the single plane can be temporarily maintained by friction. This position may be changed by overcoming the frictional force.

It shall further be noted that the holes 600 in the pressure element 6' can be located at another position, for example, the holes can be aligned circumferentially with the rod channel, so that a pivot plane for the bone anchoring element 1' can be perpendicular to the longitudinal axis of the rod channel. More than two opposite holes 600 can also be provided to facilitate selective uniplanar movement in more than a single pivot plane. For example, four holes can be provided, where two holes are positioned circumferentially at the legs of the pressure element 6', and two additional holes are aligned circumferentially with the rod channel. The receiving part 5' may have threaded through holes 58' at corresponding positions. The head 3' may also have more than the two recesses 31.

In a further modification, the head 3 may have, at its free end surface, one or more indication features (not shown in the figures) that indicate the circumferential position of the recesses 31. This may more easily facilitate the alignment of the recesses 31 with the threaded holes 58' of the receiving part 5' when the head 3' is in the receiving part 5'.

With the bone anchoring device according to the third and fourth embodiments, a modular system can be provided which permits or more easily facilitates assembly of a variety of bone anchoring devices out of only a few parts.

Further modifications of the above-described embodiments are also conceivable. In particular, the shape of the parts is not limited to the detailed shapes as shown in the figures. Deviations may be possible and encompassed by the disclosure. Although in the embodiments discussed, two threaded through holes and two corresponding restriction elements are shown, only one threaded through hole and one restriction element may be sufficient.

Instead of the locking member 8 being a set screw, all other kinds of locking assemblies known in the art may be used. For the bone anchoring element, all types of bone anchoring elements that are suitable for anchoring in bone or a vertebra, such as bone screws, bone nails, etc., may be used. Furthermore, as used in the present specification and the appended claims, the term "rod" shall be understood as including any elongate member, regardless of the cross-sectional shape of the elongate member. Specifically, a spinal stabilization rod as used herein may have a substantially circular, oval, or angular cross-section. Such cross-section may further vary along a length of the rod. The rod may be stiff or flexible.

Moreover, the accommodation space of the receiving part and the pressure element may have a design that allows pivoting of the bone anchoring element to a greater pivot angle to one side compared to other sides.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. A bone anchoring device for coupling a rod to a bone, the bone anchoring device comprising:

an anchoring element comprising a shank for anchoring to the bone and a head;

a receiving part having a first end, a second end, a central axis extending between the first and second ends, a channel at the first end for receiving the rod, an accommodation space at the second end for accommodating the head of the bone anchoring element, and at least one hole that extends through the receiving part in a direction transverse to the central axis;

a pressure element positionable in the receiving part, the pressure element configured to extend into the channel to engage the rod and to engage and exert pressure on the head to lock an angular position of the head relative to the receiving part; and at least one restriction element selectively insertable into the hole of the receiving part;

wherein when the pressure element is in the receiving part, the head is insertable from the second end of the receiving part into the accommodation space; and wherein the restriction element is movable in the hole in the direction transverse to the central axis from a first position where the head is pivotable polyaxially relative to the receiving part, to a second position where a first surface of the restriction element cooperates with a second surface of the pressure element to urge the pressure element against the head to restrict the pivotability of the head in at least one direction relative to the central axis.

2. The bone anchoring device of claim 1, wherein the restriction element comprises a thread configured to engage a corresponding thread in the hole of the receiving part.

3. The bone anchoring device of claim 1, wherein the pressure element is monolithic, and wherein the restriction element is configured to extend laterally into the pressure element in the receiving part.

4. The bone anchoring device of claim 1, wherein the cooperation between the first and second surfaces is configured to urge the pressure element against the head with a sufficient force to lock the head in the receiving part.

5. The bone anchoring device of claim 1, wherein at least one of the first or second surfaces is inclined relative to the central axis.

6. The bone anchoring device of claim 1, wherein at the second position, the restriction element is configured to restrict the pivotability of the head to a single plane, such that movement between the head and the receiving part is restricted to uniplanar movement.

7. The bone anchoring device of claim 6, wherein the single plane includes the central axis and a longitudinal axis of the channel for the rod.

8. The bone anchoring device of claim 1, wherein at the second position, the restriction element is configured to prevent pivoting of the head in every direction relative to the central axis, such that the head and the receiving part form a monoaxial device.

9. The bone anchoring device of claim 1, wherein the pressure element is configured to be held in the receiving part while the restriction element is spaced apart from the hole, and wherein the head can be locked relative to the receiving part without assembling the restriction element to the receiving part.

10. The bone anchoring device of claim 1, wherein a longitudinal axis of the hole is perpendicular to the central axis.

11. The bone anchoring device of claim 1, wherein the restriction element comprises a portion that is configured to be broken off after the restriction element assumes the second position.

12. The bone anchoring device of claim 1, wherein the receiving part is a first receiving part configured to receive a first rod, wherein the bone anchoring device further comprises a second receiving part for receiving a second rod, and wherein the second receiving part is connectable to the first receiving part via a connection element that is engageable with the second receiving part and the hole of the first receiving part.

13. A bone anchoring device for coupling a rod to a bone, the bone anchoring device comprising:

an anchoring element comprising a shank for anchoring to the bone and a head;

a receiving part having a first end, a second end, a central axis extending between the first and second ends, a channel at the first end for receiving the rod, an accommodation space at the second end for accommodating the head of the bone anchoring element, and at least one threaded hole that extends through the receiving part in a direction transverse to the central axis;

a pressure element positionable in the receiving part, the pressure element configured to engage and exert pressure on the head to lock an angular position of the head relative to the receiving part; and at least one restriction element selectively insertable into the threaded hole of the receiving part;

wherein when the restriction element is spaced apart from the threaded hole, the pressure element is configured to be held in and prevented from being removed from the receiving part; and wherein the restriction element is movable in the threaded hole in the direction transverse to the central axis from a first position where the head is pivotable polyaxially relative to the receiving part, to a second position where a first surface of the restriction element cooperates with a second surface of the pressure element to urge the pressure element against the head to restrict the pivotability of the head in at least one direction relative to the central axis.

14. The bone anchoring device of claim 13, wherein at the second position, the restriction element is configured to restrict the pivotability of the head to a single plane, such that movement between the head and the receiving part is restricted to uniplanar movement.

15. A method for coupling a rod to a bone using a bone anchoring device comprising an anchoring element comprising a shank for anchoring to the bone and a head, a receiving part having a first end, a second end, a central axis extending between the first and second ends, a channel at the first end for receiving the rod, an accommodation space at the second end for accommodating the head of the bone anchoring element, and at least one hole that extends through the receiving part in a direction transverse to the central axis, a pressure element positionable in the receiving part, the pressure element configured to extend into the channel to engage the rod and to engage and exert pressure on the head to lock an angular position of the head relative to the receiving part, at least one restriction element selectively insertable into the hole of the receiving part, and a locking element, the method comprising:

inserting the head from the second end of the receiving part into the accommodation space when the pressure element is in the receiving part;

selectively inserting the restriction element into the hole of the receiving part, wherein when the restriction element is inserted into the hole of the receiving part, the restriction element is movable in the hole in the direction transverse to the central axis from a first position where the head is pivotable polyaxially relative to the receiving part, to a second position where a first surface of the restriction element cooperates with a second surface of the pressure element to urge the pressure element against the head to restrict the pivotability of the head in at least one direction relative to the central axis;

adjusting the receiving part relative to the head;

inserting the rod into the channel of the receiving part; and advancing the locking element into the channel to lock the head and the rod relative to the receiving part.

* * * * *